US010010502B2

(12) United States Patent
Leahy et al.

(10) Patent No.: US 10,010,502 B2
(45) Date of Patent: Jul. 3, 2018

(54) DEVICE THAT DELIVERS A SUSTAINED LOW-DOSE OF A MYOPIA-SUPPRESSING DRUG, WHILE PRESERVING PUPILLARY FUNCTION AND ACCOMMODATION

(71) Applicant: AMORPHEX THERAPEUTICS LLC, Reno, NV (US)

(72) Inventors: Charles D. Leahy, Concord, MA (US); Edward J. Ellis, Lynnfield, MA (US)

(73) Assignee: AMORPHEX THERAPEUTICS LLC, Reno, NV (US)

( * ) Notice: Subject to any disclaimer, the term of this patent is extended or adjusted under 35 U.S.C. 154(b) by 0 days.

(21) Appl. No.: 15/159,357

(22) Filed: May 19, 2016

(65) Prior Publication Data

US 2016/0338947 A1 Nov. 24, 2016

Related U.S. Application Data

(60) Provisional application No. 62/163,534, filed on May 19, 2015.

(51) Int. Cl.
*A61K 9/00* (2006.01)
*A61K 47/48* (2006.01)
*A61K 47/12* (2006.01)
*A61K 31/46* (2006.01)
*A61K 31/473* (2006.01)
*A61K 31/522* (2006.01)
*A61K 31/7076* (2006.01)
*A61K 47/32* (2006.01)
*A61K 47/34* (2017.01)
*G02B 1/04* (2006.01)
*G02C 7/04* (2006.01)

(52) U.S. Cl.
CPC ............ *A61K 9/0051* (2013.01); *A61K 31/46* (2013.01); *A61K 31/473* (2013.01); *A61K 31/522* (2013.01); *A61K 31/7076* (2013.01); *A61K 47/12* (2013.01); *A61K 47/32* (2013.01); *A61K 47/34* (2013.01); *G02B 1/043* (2013.01); *G02C 7/04* (2013.01)

(58) Field of Classification Search
CPC ...... A61K 31/46; A61K 9/0051; A61K 47/32; A61K 47/34; G02B 1/043; G02C 7/04
See application file for complete search history.

(56) References Cited

U.S. PATENT DOCUMENTS

| 3,416,530 | A | 12/1968 | Ness |
| 3,618,604 | A | 11/1971 | Ness et al. |
| 3,626,940 | A | 12/1971 | Zaffaroni et al. |
| 3,828,777 | A | 8/1974 | Ness |
| 3,845,201 | A | 10/1974 | Haddad et al. |
| 3,845,770 | A | 11/1974 | Theeuwes et al. |
| 3,867,519 | A | 2/1975 | Michaels |
| 3,961,628 | A | 6/1976 | Arnold |
| 3,962,414 | A | 6/1976 | Michaels |
| 3,963,025 | A | 6/1976 | Whitaker et al. |
| 3,993,071 | A | 11/1976 | Higuchi et al. |
| 3,995,635 | A | 12/1976 | Higuchi et al. |
| 4,014,335 | A | 3/1977 | Arnold |
| 4,039,662 | A | 8/1977 | Hecht et al. |
| 4,135,514 | A | 1/1979 | Zaffaroni et al. |
| 4,164,559 | A | 8/1979 | Miyata et al. |
| 4,179,497 | A | 12/1979 | Cohen et al. |
| 4,186,184 | A | 1/1980 | Zaffaroni |
| 4,190,642 | A | 2/1980 | Ben-Dor |
| 4,281,654 | A | 8/1981 | Shell et al. |
| 4,343,787 | A | 8/1982 | Katz |
| 4,346,709 | A | 8/1982 | Schmitt |
| 4,402,695 | A | 9/1983 | Wong |
| 4,479,818 | A | 10/1984 | Shell et al. |
| 4,592,752 | A | 6/1986 | Neefe |
| 4,650,843 | A | 3/1987 | Yokoyama et al. |
| 4,668,506 | A | 5/1987 | Bawa |
| 4,730,013 | A | 3/1988 | Bondi et al. |
| 4,863,457 | A | 9/1989 | Lee |
| 4,910,015 | A | 3/1990 | Sung et al. |
| 5,057,585 | A | 10/1991 | Agou et al. |
| 5,137,728 | A | 8/1992 | Bawa |
| 5,147,647 | A | 9/1992 | Darougar |
| 5,252,318 | A | 10/1993 | Joshi et al. |
| 5,284,843 | A | 2/1994 | Stone et al. |
| 5,322,691 | A | 6/1994 | Darougar et al. |

(Continued)

FOREIGN PATENT DOCUMENTS

CN 101049287 10/2007
EP 0262893 4/1988

(Continued)

OTHER PUBLICATIONS

D. Lisa Land, et al.; "Sizes and Shapes of Conjunctival Inserts"; ICLC, vol. 21 Nov./Dec. 1994; pp. 212-217.
Marco Fabrizio Saettone; :Solid Polymeric Inserts/Disks as Drug Devices; Biopharmaceutics of Ocular Drug Delivery; pp. 61-79.
J. Zhao et al., "Study on retinal dopamine transporter in form deprivation myopia using the radiopharmaceutical tracer $^{99m}$Tc-TRODAT-1", Nucl Med Commun. Jun. 28, 2010;31:910-5.
Lee YH, Lee VH, "Formulation influence on ocular and systemic absorption of topically applied atenolol in the pigmented rabbit", J Ocul Pharmacol 1993; 9:47-58. Accepted for Publication Dec. 2, 1992.
Phillip Hoyng & Luc van Beek, "Pharmacologic Therapy for Glaucoma", 59 DRUGS 411, 423-24 (Mar. 2000).
Sihvola P, et al., "Practical Problems in the Use of Ocusert-Pilocarpine Delivery System", Acta Ophthalmol. (Copenh.), 58 (6) 933-937, Mar. 17, 1980.

(Continued)

*Primary Examiner* — Anna Falkowitz
(74) *Attorney, Agent, or Firm* — Leason Ellis LLP

(57) ABSTRACT

A non-degradable topical ocular drug delivery device includes about 0.001% to about 10% w/w of at least one myopia-suppressing agent complexed with an immobile acid within a crosslinked polymer matrix. The cross-linked polymer matrix is configured to deliver the least one myopia-suppressing agent over an extended period of time at a concentration and rate that controls myopia progression while preserving pupillary function and accommodation.

26 Claims, 7 Drawing Sheets

(56) References Cited

U.S. PATENT DOCUMENTS

| | | |
|---|---|---|
| 5,336,797 A | 8/1994 | McGee et al. |
| 5,472,436 A | 12/1995 | Fremstad |
| 5,556,633 A | 9/1996 | Haddad et al. |
| 5,571,823 A | 11/1996 | Stone et al. |
| 5,574,044 A | 11/1996 | Thompson et al. |
| 5,607,696 A | 3/1997 | Rivera et al. |
| 5,609,885 A | 3/1997 | Rivera et al. |
| 5,612,027 A | 3/1997 | Galin et al. |
| 5,660,851 A | 8/1997 | Domb |
| 5,707,643 A | 1/1998 | Ogura et al. |
| 5,756,508 A | 5/1998 | Thompson et al. |
| 5,770,669 A | 6/1998 | Robertson et al. |
| 5,814,638 A | 9/1998 | Lee et al. |
| 5,858,996 A | 1/1999 | Tsao |
| 5,874,500 A | 2/1999 | Rhee et al. |
| 5,977,428 A | 11/1999 | Bozigian et al. |
| 6,018,033 A | 1/2000 | Chen et al. |
| 6,196,993 B1 | 3/2001 | Cohan et al. |
| 6,217,896 B1 | 4/2001 | Benjamin |
| 6,264,971 B1 | 7/2001 | Darougar et al. |
| 6,413,245 B1 | 7/2002 | Yaacobi et al. |
| 6,413,540 B1 | 7/2002 | Yaacobi |
| 6,416,777 B1 | 7/2002 | Yaacobi |
| 6,482,531 B1 | 11/2002 | Timmons et al. |
| 6,669,950 B2 | 12/2003 | Yaacobi |
| 6,713,081 B2 | 3/2004 | Robinson |
| 6,808,719 B2 | 10/2004 | Yaacobi |
| 6,986,900 B2 | 1/2006 | Yaacobi |
| 7,094,226 B2 | 8/2006 | Yaacobi |
| 7,181,287 B2 | 2/2007 | Greenberg |
| 8,167,855 B2 | 5/2012 | Leahy et al. |
| 8,715,712 B2 | 5/2014 | De Juan, Jr. et al. |
| 8,883,214 B2 | 11/2014 | Wildsoet et al. |
| 2002/0058068 A1 | 5/2002 | Houze et al. |
| 2002/0197300 A1 | 12/2002 | Schultz et al. |
| 2004/0176749 A1 | 9/2004 | Lohmann |
| 2004/0247681 A1 | 12/2004 | Ellis et al. |
| 2005/0013845 A1 | 1/2005 | Warren et al. |
| 2005/0064010 A1 | 3/2005 | Cooper et al. |
| 2005/0181018 A1 | 8/2005 | Peyman |
| 2006/0198892 A1 | 9/2006 | Ellis et al. |
| 2007/0112318 A1 | 5/2007 | Leahy et al. |
| 2007/0233037 A1 | 10/2007 | Gifford et al. |
| 2007/0254914 A1 | 11/2007 | Wu et al. |
| 2008/0145406 A1 | 6/2008 | Asgharian et al. |
| 2008/0171072 A1 | 7/2008 | Burczynski |
| 2010/0114309 A1 | 5/2010 | de Juan, Jr. et al. |
| 2010/0178315 A1* | 7/2010 | Ellis ............... A61K 9/0004 424/427 |
| 2010/0233241 A1* | 9/2010 | Leahy ............. A61F 9/0017 424/428 |
| 2010/0247606 A1 | 9/2010 | Robinson et al. |
| 2014/0036225 A1* | 2/2014 | Chehab ............ A61K 31/46 351/159.02 |
| 2014/0276478 A1* | 9/2014 | Liao ............... A61K 31/27 604/290 |
| 2015/0079179 A1* | 3/2015 | Cook .............. A61K 9/5138 424/489 |
| 2015/0366854 A1 | 12/2015 | Ostrow et al. |
| 2016/0009705 A1 | 1/2016 | Ostrow et al. |

FOREIGN PATENT DOCUMENTS

| | | |
|---|---|---|
| EP | 0834308 | 4/1998 |
| EP | 0923918 | 6/1999 |
| EP | 1473003 | 11/2004 |
| EP | 2 693 259 | 2/2014 |
| FR | 2 661 832 | 11/1991 |
| GB | 850390 | 10/1960 |
| GB | 2341185 | 3/2000 |
| JP | Hei 6-273702 A | 9/1994 |
| JP | 2741624 B2 | 4/1998 |
| JP | Hei 11-151263 A | 6/1999 |
| WO | WO 01/32140 | 5/2001 |
| WO | WO 03/013477 | 2/2003 |
| WO | WO 03/020172 | 3/2003 |
| WO | WO 2007/034140 | 3/2007 |
| WO | WO2012161655 | 11/2012 |
| WO | WO-2012161655 A1 * | 11/2012 ............ A61K 31/46 |
| WO | WO 2014151492 | 9/2014 |

OTHER PUBLICATIONS

Holden BA, Fricke TR, Wilson DA, Jong M, Naidoo KS, Sankaridurg P, Wong TY, Naduvilath TJ, Resnikoff S, "Global Prevalence of Myopia and High Myopia and Temporal Trends from 2000 through 2050", Ophthalmology, May 2016 vol. 123, Issue 5, pp. 1036-1042.

Holden B, Sankaridurg P, Smith E, Aller T, Jong M, He M., "Myopia, an underrated global challenge to vision: where the current data takes us on myopia control", Eye (London, England) 2014; 28(2): 142-6. Published Online Dec. 20, 2013.

Lin, L.L., Shih, Y.F., Hsiao, C.K., Chen, C.J., Lee, L.A., and Hung, P.T., "Epidemiologic study of the prevalence and severity of myopia among schoolchildren in Taiwan in 2000", JFormos. Med. Assoc. 100:684-691, Jul. 10, 2001.

Vitale, S., Sperduto, R.D., and Ferris, F.L., 3rd, "Increased prevalence of myopia in the United States between 1971-1972 and 1999-2004", Arch. Ophthalmol. 127:1632-1639, Dec. 2009.

Jensen, H., "Myopia in teenagers. An eight-year follow-up study on myopia progression and risk factors", Acta. Ophthalmol. Scand. 73:389-393, Oct. 1995.

Liang, C.L., Yen, E., Su, J.Y., Liu, C., Chang, T.Y., Park, N., Wu, M.J., Lee, S., Flynn, J.T., and Juo, S.H., "Impact of family history of high myopia on level and onset of myopia", Invest. Ophthalmol. Vis. Sci. 45:3446-3452, Oct. 2004.

Walline JJ, Jones LA, Sinnott LT, "Corneal reshaping and myopia progression", Br J Ophthalmol May 4, 2009;93:1181-1185.

Dorothy S. P. Fan DSP, Lam DSC, Chan CKM, Fan AH, Cheung EYY, Rao SK, "Topical Atropine in Retarding Myopic Progression and Axial Length Growth in Children with Moderate to Severe Myopia: A Pilot Study", Jpn J Ophthalmol 2007;51:27-33. Accepted Aug. 30, 2006.

Saw SM1, Gazzard G, Au Eong KG, Tan DT, "Myopia: attempts to arrest progression", Br J Ophthalmol. Nov. 2002;86(11):1306-11.

Yin GC, Gentle A, McBrien NA, "Muscarine antagonist control of myopia: A molecular search for the M1 receptor in chicks", Mol Vis. Aug. 19, 2004;10:787-93.

Russo A, Semeraro F, Romano MR, Mastropasqua R, Dell'Omo R, Costagliola C., "Myopia onset and progression: can it be prevented?", Int Ophthalmol (2014) 34:693-705. Published Online Sep. 17, 2013.

Bitzer M, Kovacs B, Feldkaemper M, Schaeffel F., "Effects of muscarinic antagonists on ZENK expression in the chicken retina", Exp Eye Res 2006;2:379-388. Available online Sep. 6, 2005.

Stone RA, Lin T, Laties AM, "Muscarinic antagonist effects on experimental chick myopia", Exp Eye Res 1991 ;52:755-758. Accepted Sep. 10, 1990.

Siatkowski RM, Cotter S, Miller JM, et al., "Safety and efficacy of 2% pirenzepine ophthalmic gel in children with myopia: a 1-year, multicenter, double-masked, placebo-controlled parallel study", Arch Ophthalmol, Nov. 2004;122:1667-1674.

Taylor BJ, Smith PJ, Brook CG, "Inhibition of physiological growth hormone secretion by atropine", Clin Endocrinol 1985;22: 497-501. Accepted Oct. 22, 1984.

Casanueva FF, Villanueva L, Diaz Y, Devesa J, Fernandez-Cruz A, Schally AV, "Atropine selectively blocks GHRH-induced GH secretion without altering LH, FSH, TSH, PRL and ACTH/cortisol secretion elicited by their specific hypothalamic releasing factors", Clin Endocrinol, May 27, 1986;25:319-323.

McBrien NA, Moghaddam HO, Reeder AP, "Atropine reduces experimental myopia and eye enlargement via a nonaccommodative mechanism", Invest Ophthalmol Vis Sci, Jan. 1993; 34: 205-215.

Song YY1, Wang H, Wang BS, Qi H, Rong ZX, Chen HZ, "Atropine in ameliorating the progression of myopia in children with mild to moderate myopia: a meta-analysis of controlled clinical

(56) References Cited

OTHER PUBLICATIONS trials", J Ocul Pharmacol Ther. Aug. 2011;27(4):361-8. doi: 10.1089/jop.2011.0017. Epub Jun. 7, 2011.

Huang, J, Wen D, Wang Q, McAlinden C, Flitcroft I, Chen H, Saw CM, Chen H, Bao F, Zhao Y, Hu L, Li X, Gao R, Lu W, Du Y, Junag, Z, Yu A, Lian H, Jiang O, Yu Y, Qu J, "Efficacy Comparison of 16 Interventions for Myopia Control in Children A Network Meta-analysis", [published online Jan. 12, 2016]. Ophthalmology. DOI:http://dx.doi.org/10.1016/j.ophtha.2015.11.010, Accessed Mar. 26, 2016.

KL Loh, Q Lu, D Tan, A Chia, "Risk Factors for Progressive Myopia in the Atropine Therapy for Myopia Study", American Journal of Ophthalmology, May 2015 vol. 159, Issue 5, pp. 945-949.

Ciolino JB, Hoare TR, Iwata NG, Irmgard Behlau, Dohlman CH, Langer R, Kohan DS, "A Drug-Eluting Contact Lens", Investigative Ophthalmology and Visual Science. Jul. 2009;50:3346-3352.

Ciolino JB, Stefanescu CF, Ross AE, Salvador-Culla B, Cortez P, Ford EM, Wymbs KA, Sprague SL, Mascoop DR, Rudina SS, Trauger SA, Cade F, Kohane DS, "In vivo performance of a drug-eluting contact lens to treat glaucoma for a month", Biomaterials 35 (2014) 432-439. Available online Oct. 4, 2013.

Chia A, Chua WH, Cheung YB, et al., "Atropine for the treatment of childhood myopia: Safety and efficacy of 0.5%, 0.1% and 0.01% doses (Atropine for Treatment of Myopia 2)", Ophthalmology 2012;119:347-354. Accepted Jul. 20, 2011.

V.A. Barathi VA, Beuerman RW, "Molecular mechanisms of muscarinic receptors in mouse scleral fibroblasts: Prior to and after induction of experimental myopia with atropine treatment", Molecular Vision Mar. 9, 2011; 17:680-692.

K. Trier et al., "Systemic 7-methylxanthine in retarding axial eye growth and myopia progression: a 36-month pilot study", J Ocul Biol Dis Infor. Dec. 2008; 1(2-4):85-93.

L. Jiang et al., "Effects of Dopaminergic Agents on Progression of Naturally Occurring Myopia in Albino Guinea Pigs (*Cavia Porcellus*)", Investigative Ophthalmology & Visual Science Nov. 2014, vol. 55, 7508-7519. doi:10.1167/iovs.14-14294.

Fredholm et al., "International Union of Pharmacology. XXV. Nomenclature and Classification of Adenosine Receptors", Pharmacol Rev 53:527-552, Dec. 2001.

M Malhotra and D. K. Majumdar, "Permeation through cornea", Indian Journal of Experimental Biology, vol. 39, Jan. 2001, pp. 11-24.

Leahy CD, Ellis EE, Ellis JY, Crawford KC, "Efficacy of a Topical Ocular Drug Delivery Device (TODDD) for the treatment of glaucoma by telemetric measurement of IOP in the normal rabbit", Investigative Ophthalmology and Visual Science Suppl vol. 48, Program No. 5816, May 2007.

Claus-Michael Lehr et al., "Improved Ocular Penetration of Gentamicin by Mucoadhesive Polymer Polycarbophil in the Pigmented Rabbit", Invest. Ophthalmol. Vis. Sci., 35, 2809-2814 (1994). Accepted Dec. 16, 1993.

Loughman, J, Flitcroft, DI., "The acceptability and visual impact of 0.01% atropine in a Caucasian population", Br J Ophthalmol doi:10.1136/bjophthalmol-2015-307861. Published Online Feb. 22, 2016.

Mitra, Ashim K., "Ophthalmic Drug Delivery Systems", Marcel Dekker, Inc., vol. 130, New York, 1993.

Huang, Hsiu-Mei et al., "The Association between Near Work Activities and Myopia in Children—A Systematic Review and Meta-Analysis", PLOS ONE, Published Oct. 20, 2015, pp. 1-15.

\* cited by examiner

DEVICE THAT DELIVERS A SUSTAINED LOW-DOSE OF A MYOPIA-SUPPRESSING DRUG, WHILE PRESERVING PUPILLARY FUNCTION AND ACCOMMODATION

CROSS-REFERENCE TO RELATED APPLICATION

This application is based on and claims priority to U.S. Provisional Patent Application 62/163,534, filed May 19, 2015, the entire contents of which is incorporated by reference herein as if expressly set forth in its respective entirety herein.

TECHNICAL FIELD

The present invention is a non-degradable topical ocular device, shaped to fit the surface of the sclera away from the cornea, with a matrix designed to provide continuous drug delivery of a myopia-suppressing drug—such as a muscarinic blocking agent, dopamine agonist, and/or an adrenergic antagonist—to the eye, at sustained low-dose drug concentrations that can moderate the progression of myopia, while minimizing local and systemic adverse effects. In particular, the compositions disclosed in the present invention comprise sustained release matrix devices incorporating methacrylic acid or similar moieties to complex with the nitrogen in myopia-suppressing agents, including anti-muscarinic agents, such as, atropine and pirenzepine, to provide greater control of effective drug release rate over a period of weeks or months, especially at very low doses. The combination of large size and comfort of the device enable the long duration of release, for weeks or months, of the myopia-suppressing agent from the same device without removing it from the eye. Another advantage of this invention is its support of patient compliance, which can translate into improved therapeutic efficacy. The design and material combinations of this comfortable device, which can be designed with more mass for drug loading and long term delivery than smaller ocular devices, for example a contact lens, and yet be comfortable and worn continuously, provide a novel alternative, with improved efficacy, compliance and safety, when compared to administration of the same drugs by eye drop administration.

BACKGROUND

Myopia (short or near-sightedness) is an eye condition where distant objects cannot be seen clearly. It can be optically corrected (not cured) with spectacles, contact lenses or refractive surgery. Myopia affects many children as they enter school-age, and is becoming a major public health issue. The worldwide growing prevalence seems to be associated with increasing educational pressures, life-style changes involving more near work, and a reduction in the time that children spend outdoors. It is estimated that the current number of 1.45 billion people with the condition will grow to a staggering 2.5 billion by 2020. The rate of myopia has doubled in the US since the 1970s to almost half of teenagers, and the number of high myopes has risen eight-fold. In Taiwan and Singapore, the prevalence of myopia is 20%-30% among 6-7-year olds and as high as 84% in high-school students in Taiwan.

The onset of myopia at an early age brings with it the likelihood of life-long eye care, and affects quality of life, education and learning, both when left undetected and in between periodic corrective prescription updates for this continually progressive condition. Myopia also doubles the risk of serious ocular health problems such as glaucoma, and retinal trauma, malfunction and detachment, which can lead to vision loss and blindness. Early onset of myopia in childhood is associated with a higher rate of progression and high myopia in adult life, and we can expect an increased prevalence of associated severe ocular complications later in life.

The identification of an effective and practical treatment will have a significant public health impact on the quickly growing prevalence of myopia and its attendant problems.

Several interventions to decrease the progression of myopia have been proposed and investigated. These include devices that alter the perception of the visual environment and pharmacological treatments. There is no conclusive evidence thus far that any alteration of the pattern of spectacle wear, bifocals, standard contact lenses, or the use of ocular hypotensives effectively retard the progression of myopia.

More recently, efforts have been underway on two fronts to develop and commercialize contact lenses with specific designs to address the peripheral retinal defocus implicated as a factor in the progression of myopia. One is the use of orthokeratology lenses, currently approved for the temporary correction of myopia by flattening the front of the eye, and worn by a very small number of patients to temporarily correct myopia during the day by reshaping the front of the eye after overnight wear of the lenses. It has also been shown that myopia progression seems to be retarded with the use of such lenses. However, this expensive process involves rigid lenses that must be worn overnight, at an increased risk of infection. The optimal optical properties have yet to be worked out as far as controlling the myopia progression in a given patient with a given prescription, as each will likely be a custom-made lens. As these are not approved by the FDA for treating myopia progression, prescribing them as such is off-label, presenting greater risk for the patient and the practitioner who prescribes them as lenses to sleep in for years. There is also some evidence that treating the lower levels of myopia with orthokeratology, up to −2.00 diopters, can actually increase the rate of myopia progression. This is precisely the population that is the desired target of myopia progression control, with the goal of stopping or slowing the condition as early as possible.

The other area of development of lenses that do not reshape the eye, but are designed with various optical features in their peripheries to theoretically affect the associated peripheral retinal imaging and thereby reduce the progression of myopia. These tend to be soft lenses, and are similar to commercially available soft bifocal or multifocal contact lenses, and any distinguishing treatment effects or improved efficacy of these proprietary designs have yet to be demonstrated sufficiently. These devices also suffer from inexact knowledge of specific effective parameters, such as the most effective size or strength of the varied power zones of the lens. The sources of this issue are the unknown effects of exact parameter changes, and the assumption that these zones could be projected directly to the purported treatment area of the retina. The fact is that the lenses must sit on the cornea, so that the different specific lens optical areas do not actually correspond, or project, directly to the desired peripheral defocus areas on the retina. Being at the plane of the cornea, the lenses do not sit at the entrance pupil of the eye and therefore do not optically project their different zones directly to the presumed areas of treatment on the retina. These lenses are intended to be worn virtually all day, every day, which of course not all patients will be able to do for a number of reasons, such as allergies, dryness and discomfort symptoms, and lifestyle activities.

The soft bifocal and multifocal contact lenses also blur the distance vision, due to the constant presence of the near prescription powers in front of the pupil, and blur the near vision, due to the constant presence of the distance prescription power in front of the pupil simultaneously. Unlike bifocal or progressive multifocal eyeglasses, therefore, the patient is constantly looking through the "other" prescription as well as the one they need at the moment, resulting in glare and ghosting at distance from the near prescription, and decreased clarity at near, from the presence of the distance prescription. This is the primary reason for the limited penetration of such products into the market of seventy-plus million presbyopes in the U.S. who do not want to use bifocal glasses or "readers" that they are so dependent on. And the limited patient acceptance of such soft contact lenses has been unpredictably random, resulting in disappointing adoption and use of these lenses, both by the patients and by the people fitting them. The clinical reality is that the vast majority of even those patients who do accept this wearing modality end up wearing lenses that are "pushed" a little, for better distance vision in one eye and better near vision in the other. This could not logically be done in treating myopia, as one would not want to undertreat one eye by giving a less than optimal treatment optical system. The resulting blur of having the full "bifocal" effect in front of both eyes, most likely more symptomatic at distance, would make the wearing of such bifocal lenses even less accepted, especially among children, than it is already in the over-forty presbyopic patient population. The low historical success rate of fitting such lenses and the chair time used up doing so, will continue to limit their adoption by most fitters.

Driving the efforts of most of the proposed pharmacological treatments has been the long-perceived association between excessive near work and myopia progression. Pharmaceutical agents directed at inhibiting the focusing mechanism of the eye (cycloplegic agents) attempt to block near focus by paralyzing the accommodation, or focusing, ability of the eye. Muscarinic antagonists, predominantly atropine, have been available for a century for very temporary application to the eye, such as for dilating the eye for examination of the interior of the eye or for short term inhibition of inflammation of the iris (tissue that forms the pupil) following ocular trauma, or for paralyzing accommodation, the ability of the eye to focus up close. This paralysis allows a more objective determination of refractive error without the focusing mechanism (accommodation) being active. The intuitive and conventional wisdom connecting excessive near work and accommodation to the development and progression of myopia has led to several randomized clinical trials investigating this application of historically established clinical doses of atropine to treat myopia by causing cycloplegia. These studies have demonstrated that the rate of progression of myopia is indeed lower in children given atropine eye drops than those given placebo.

In fact, this substantial proportional reduction in the progression of the myopia condition compares quite well with the pharmaceutical treatment of other chronic progressive diseases. The historically clinically used drop concentrations of 0.5% and 1.0% have been shown to be more effective than experimental lower doses of 0.05%, 0.1% and 0.25%, yielding 0.2 or less diopters/year myopia progression vs. 2-4 times that amount of progression occurring with the use of the lower doses. And appropriately, while many approved drugs have been studied far more in adults than children, in the case of myopia, a condition needing treatment in childhood, studies with atropine have focused on treating children in their study populations. This is important, as children are particularly vulnerable to the systemic and local side effects of higher doses of these agents. These efforts and results using drop delivery have pointed to the need to deliver the pharmaceutical agent at an effective dose without causing excessive side effects to which children are prone.

In fact, most comparative and review studies, including a thorough meta-analysis of randomized controlled trials, have showed that such pharmacological treatment of myopia progression has the greatest efficacy of various treatments tried, including treatments using special eyeglasses and contact lenses.

However, these clinical doses of atropine eye drops lead to pupil dilation and cycloplegia levels that render long-term treatment unacceptable to patients and practitioners. When applied to the long-term treatment of myopia patients, it is not desirable to have a markedly dilated or fixed pupil, nor is it desirable to completely inhibit the focusing ability of the patient. There is a need to maintain a steady-state of functioning pupil and focusing mechanisms, without large fluctuations in function that would create annoying symptoms for the patient. Eye drop application, at whatever dose, affects both the pupil and focusing function variably over time, in a peak-trough fashion, with maximal effect shortly after drop application that slowly decreases towards zero, until the next drop application. Generally for ocular drops these effects wear off in hours or a day, leading to common prescriptions of various eye drops to be used one to a few times a day. With atropine and other anti-muscarinic agents however, one drop can yield dilation that last several days or even a week or more. Therefore progressively lower doses have been subsequently tried for myopia progression treatment due to the debilitating and unacceptable side effects of standard clinical doses for long-term treatment. In recognition of the need for less severe cycloplegia and pupil dilation, prior art teaches the use of low concentration eye drops (200610072954.9 CN 101049287 A, and Chua et al WO2012161655 A1, 2012).

However, topically instilled eye drops are rapidly diluted by tears and quickly washed away from the ocular surface, draining through the puncta. Consequently, an administered drug solution has only a brief opportunity, via a concentration gradient, to deliver drug through the cornea and sclera to the target tissue; in general, the lower the concentration of an applied drug solution, the less chance of delivering sufficient drug to be effective.

It is for these reasons that an anti-muscarinic eye drop solution can only deliver about 5% of their active to the eye. The remaining 95% may be bioavailable to cause systemic effects. Consequently, high concentration anti-muscarinic solutions may result in both local and systemic adverse effects, while low concentration formulations, may generate an insufficient concentration gradient, on the ocular surface, to deliver an effective level of drug to targeted tissue.

A more recently proposed effect of these anti-muscarinic agents relates to slowing the abnormal growth of the eyeball that occurs proportionally to the increasing myopia, as measured clinically by increased axial length of the eye. A number of researchers have proposed that receptors responsible for slowing the abnormal growth of the eyeball are in the posterior ocular tissue near or at the retina, while different receptors, acting to dilate of the pupil and the paralyze accommodation, are in anterior tissues at the ciliary body. If, as proposed, receptors are different, both in structure and in location, that would allow some drugs to act more selectively to suppress myopia progression [e.g. select anti-muscarinics, dopamine agonists, adenosine agonists] while minimally acting to dilate the pupil and paralyze accommodation. Furthermore, it follows that the topical application of a myopia-suppressing drug, if dosed appropriately, may minimize or avoid paralysis of the accommodative system while controlling myopia progression, producing a tolerable and safe treatment.

Unfortunately, with current therapy using atropine eye drops, lowering the drop concentration to reduce the cycloplegia also results in less drug delivery further back in the eye as well. So while the putative treatment effect is independent of cycloplegia, the delivery of the drug using eye drops is not. Lowering the concentration of a topical drug solution, in order to decrease cycloplegia and excessive pupillary dilation, also lowers the concentration of drug that might reach the retina. Therefore, it is not helpful for myopia control if the drug is no longer attaining effective concentration at the tissues that control myopia progression. Without continuous delivery of a low concentration of drug to the surface of the eye, the topical application of an atropine eye drop has insufficient time and drug concentration to deliver the drug to posterior receptors and optimally inhibit abnormal growth of the eyeball. The resulting clinical situation for treatment with atropine eye drops is a peak-trough drug concentration that cannot deliver a steady, highly-effective, yet tolerable, dose into the eye for myopia progression control. Because atropine has a narrow therapeutic window, daily application of eye drops is a highly variable process which may result in frequent days of under-treatment or frequent occurrences of a lasting fixed dilated pupil.

With administration via eye drops, the actual concentration of drug in the drops is not directly dictated by the pharmacodynamics, or the duration and magnitude of response at the active site. The primary determinant is the high concentration gradient of drug necessary at the ocular surface at the time of application of the drop in order to drive the drug into the eye during the short time of exposure to the delivery mechanism, before the entire drop is blinked away and what drug remains is diluted by tears. Since each drop is only present on the eye for a very short time, typically 5% or less of the drug gets into the eye from drop application, and the other 95% either spills out of the eye or gets washed down the tear drainage pathway into the nose and throat, leading to systemic absorption and, potentially, systemic side effects. With topical ocular delivery of myopia-suppressing drugs, therefore, the concentration of drug in the formulation may be far in excess of the amount of drug needed at the targeted receptors but, the exposure of the drug formulation to ocular tears and drainage dilutes the formulation and the drug is rapidly flushed away; drug exposure to the ocular surface is very brief, compared to the duration of treatment desired. Consequently, topical eye drop treatment is generally a very poor way to drive drug to posterior tissues.

That is one of the reasons macular degeneration and other back-of-the-eye diseases have as their main treatment option frequent ocular injections or surgically implanted intravitreal devices. Attempts to drive drug to the retina using drop delivery may result in excessive drug accumulation in the anterior eye tissues. In the case of atropine, this would result in unacceptable side effects of an excessively dilated pupil, limited pupil function, and inability to focus up close.

Unfortunately, the higher doses of atropine, while effective at controlling myopia progression, are associated with the substantial adverse reactions of photophobia and glare, resulting from the large fixed pupil, the inability to focus to see up close (cycloplegia), and recurrent allergic blepharitis (inflammation of the eyelids). These side effects limit the practicality of chronic treatment and hinder the adherence to therapy when using these agents applied via eye drops. Additionally, the higher doses are associated with the most substantial rebound of myopia upon cessation of treatment. Furthermore, severe long-term side effects of light induced retinal damage and cataract formation, primarily due to the more dilated pupil, are expected with the higher doses. The use of lower concentration drops has been tried in attempts to reduce these unacceptable side effects. However, it has been found that the reduction in side effects is accompanied by a corresponding reduction in efficacy for myopia control. That is not because the myopia progression reduction treatment effect is a result of the dilation of the pupil and/or the paralysis of accommodation, which occur towards the front of the inside of the eye, but simply because less drug is penetrating into the back of eye to the targeted receptors, most likely at the retina. Nevertheless, one encouraging finding is that the lower-dose treatments result in less rebound myopia progression following cessation of treatment, improving its net relative efficacy vs. standard drop doses. Patent applications have been made to provide smaller amounts of drug, including low concentration atropine solution, to Wu et al, although they do not specify the frequency of dosing necessary for their invention to be effective (US Pat Appl 20070254914 A1).

It is understood that any eye drop therapy, regardless of the concentration of the active agent in the drop, inherently includes the peak-trough delivery of eye drop instillation regimens and does not provide sustained release of a steady dose of drug to the eye. In fact, the use of drops, at any concentration, requires an excessive amount of drug in the drop relative to what actually penetrates the eye in the short time of exposure to the ocular surface. And most of the drop washes out of the eye because its volume is many times that of the tear film. The result of such washout, blinking and squeezing the eyes shut results in highly variable dosing during application. Adding to that variability is the high variability introduced by the lack of compliance with drop installation, either by missing the eye, dropping in more than one drop at a time, or forgetting to take them and missing the dosing altogether. Such variable application results in an uneven rate of peak-trough drug delivery inherent to the cyclical nature of periodic, highly variable drop applications, with long gaps of absolutely no drug delivery in between doses. While Wu et al teach to lowering drop concentration to limit the side effects of photophobia and focusing difficulties experienced with the high dose drops, the treatment regimen remains an intermittent one based on its eye drop therapy regimen. They do not teach a novel treatment approach, but simply to decrease the strength of the same treatment to a tolerable level, while sacrificing treatment efficacy.

Another approach to reduce such side effects has been to try other, more selective anti-muscarinic agents such as pirenzepine; pirenzepine is a selective M1 blocking agent and consequently, is less active at the muscarinic receptors of the pupil and ciliary body than atropine. Thus it does not dilate the pupil and cause light sensitivity nor loss of ability to focus as much as atropine, and should result in less potential long-term light-induced damage to the retina. Other novel anti-muscarinic compounds have been proposed in recognition of the desire to limit activity at the muscarinic receptors of the pupil and ciliary body while more selectively blocking specific receptor subtypes for the treatment of myopia progression. The use of such anti-muscarinic agents in the drug delivery system described in the Detailed Description of the Certain Embodiments of this invention also fall under the scope of this patent application.

In addition to anti-muscarinic agents, two other classes of drugs have shown promise in the suppression of myopia progression: dopaminergic agents and adenosine agonists.

Dopamine agents, such as dopamine agonists, apomorphine, bromocriptine, quinpirole and levodopa have been shown, in animal models, to retard myopia progression and this class offers another drug class to potentially treat this malady.

In a clinical trial with 68 myopic children, the adenosine agonist, 7-methylxanthine has been shown to reduce eye elongation and myopia progression in childhood myopia. The treatment appears to be safe and without side effects.

In a pilot placebo-controlled clinical trial, an oral dose of 400 mg of 7-methylxanthine was given to 68 myopic children. The study showed that the drug can reduce eye elongation and myopia progression in childhood myopia, with no reported adverse effects. Clearly, systemic treatment with 7-methylxanthine appears to have some effect in retarding axial elongation and myopia progression among myopic children, but these results indicate that perhaps larger doses should be tried. However, in future much-larger trials, required for regulatory approval, treating children orally, with an adenosine agonist, is likely to display some serious systemic effects in children; adenosine receptors play roles in heart regulation, in coronary blood flow and in the brain. Consequently, we anticipate a need for topical ocular delivery. The proposed device herein would eliminate or, at the very least, limit the systemic effects of adenosine agonists. Moreover, it would provide a means to assure better patient compliance. For example, a 7-methylxanthine-loaded device, where this basic drug would be complexed to a fixed acid within the polymer matrix, the drug would be mobile and therefore, would be expected to provide a topical dose to the surface of the eye over a period of weeks or months.

Regardless of drug used or drug class, it is especially important to reduce these side effects in the case of treating myopia, since the younger children, as well as those with more myopia at baseline, are the ones found to have the highest risk for progression. The same study showed that another risk factor for progression was both parents being myopic, which would be a known risk factor at the birth of the child. All indications are therefore for treatment earlier rather than later in life. Consequently, the safest treatments with minimal ocular and systemic side effects would be preferred, enabling treatment at as young an age as possible, at the first sign of myopia, commonly as early as six or eight years old, while minimizing risk to the health of the eye later in life.

While a fully dilated pupil and cycloplegia have been indeed the intended effects of standard clinical drop doses of these drugs for over a hundred years, bluntly achieving the overwhelming dilation and paralysis of focus desired for a few days or weeks, the finding that these drugs can slow the progression of myopia presents a new opportunity to apply these drugs to the eye, but in a manner that requires a far more refined delivery method than eye drops. The improved delivery is needed in order to provide long term chronic dosing with drug to the inner tissues of the eye, while simultaneously avoiding the effects traditionally and purposely achieved with the drops. The original treatment effects of the drops have thus become unwanted side effects. The pupil must remain functioning during the course of treatment for the comfort and safety of the patient, and the patients, especially the young patients that would be targeted with such treatment, must be able to change focus of their eyes. Otherwise, as has been shown, the patients will not tolerate or comply with the treatment and the doctors would not prescribe it due to the risks to the health of the eye from a constantly dilated pupil.

There exists a need therefore, to deliver the drug efficiently to the retina, the tissue where the local effect is postulated to occur, while not excessively building up drug levels more anterior in the eye, closer to the source of overwhelming periodic drop concentrations, and causing, through action in those more anterior tissues, the unwanted side effects of excessive pupil dilation and accommodative paralysis. Current eye drop technology cannot achieve this sustained, micro-dose delivery.

A number of attempts have been made to modify eye drop formulations to keep drug at the surface of the eye for more than a few minutes, to prolong its delivery into the eye It therefore is not surprising that one focus of scientists and clinicians has been on modifying lower dose atropine solutions to extend residence time of the formulation on the ocular surface. One example can be found in Lee et al, U.S. Pat. No. 5,814,638, 1998. Lee et al recognized that for the purpose of inhibiting the abnormal axial growth of the eye in myopia, it is desirable to maximize the delivery of a therapeutic agent to the vitreous humour and retina, while minimizing systemic absorption of the agent to prevent possible systemic side effects. They also remind us that ocular absorption of a therapeutic agent into the posterior chamber of the eye, as opposed to its systemic absorption, depends not only on the relevant ocular anatomy and physiology, but also on the physicochemical property of the agent and the form of the ophthalmic formulation. Their formulation discussions were confined entirely to eye drop formulations, teaching towards the improvement of in vitro physical stability and solubility, and also to the improvement of in vivo therapeutic efficacy by maximizing ocular absorption, while minimizing systemic absorption. They go on to describe the prior art of extending eye drop residence time at the surface of the eye and its effects on tissue and plasma drug levels vs. standard eye drops. Neither the described approach, nor their specific invention, that of prolonging the residence time of an eye drop, however, teach away from very periodic applications of necessarily large amounts of drug in relation to what is needed at the active site.

All of these efforts to prolong residence time of drops at the ocular surface provide a minimal widening of the peaks of the peak-trough pattern of dosing drug, but are not truly sustained low dose delivery.

Additionally, the application of a clinically practical drop of any concentration involves a volume far greater than that of the total amount of tears on the surface of the eye, and invariably overwhelms the tear film and flows out of the eye and systemically through the tear drainage and the nose and throat. It would be difficult, therefore, even given a prolonged drop formulation, to provide an adequately controlled, low variability, sustained delivery rate of drug to the ocular tissues with eye drop therapy. This mode of delivery cannot provide the restricted range of an anti-muscarinic drug needed to balance efficacy and tolerable side effects, on a consistent basis during long term therapy. And, while the clinical use of dopamine or adenosine agonists lag significantly behind the use of anti-muscarinic agents, a similar need for an adequately controlled, sustained delivery rate of drug can be anticipated, in order to minimize local and systemic adverse effects and improve patient compliance.

With proposed anti-muscarinic ocular therapies for myopia progression, there is a clear need to deliver small enough doses to avoid side effects from the enlarged pupil and the inability to see up close, while getting enough drug into the eye, particularly to the retina and choroid, for adequate efficacy. Likewise, we anticipate a clear need to deliver sustained small doses for other drug classes, in order to deliver drug posteriorly, while avoiding local and systemic adverse effects.

In general, it is difficult to get a drug to penetrate the eye from the bloodstream; systemic doses (oral, IV, IM, etc.) of a drug require a high-enough concentration to get the drug through the blood-retina barrier. Systemic administration of a drug potentially exposes the patient to serious systemic adverse effects. Therefore, the vast majority of drug administration to the eye for a long time has been in the form of eye drops, and more recently, for treatment at the back of the eye, in the form of far more invasive direct, repeated injections or surgical implantation of a drug delivery device. Eye drops must be loaded with excessive drug quantities than is required at the site of treatment inside the eye, in order to drive the drug into the eye during the short time the drop is at the surface of the eye. This excess drug is often the source of the undesirable ocular and systemic side effects experienced. As with many chronic ocular conditions, such as glaucoma, inflammation, infection and degenerations, the prior art and science have led the field to conclude that low dose, sustained drug delivery is aspired to as the ideal method of treating most chronic ocular conditions. And the only non-invasive way to get low dose drug into the eye in a sustained rate is to have a source of drug at or near the surface of the eye most or all of the time, in order to maintain a constant concentration gradient of available drug to drive the drug into the eye. This would allow sustained treatment at effective doses at the desired site of action, while avoiding ocular and systemic side effects from the comparatively high concentration loading necessary with drops. While injections, or implantation of a device, under the surface layers or right through into the interior vitreous of the eye provide access of the drug to posterior tissues, these procedures must be repeated several times a year and present significant risk of infection, uveitis, retinal separation, and other serious adverse effects There clearly exists a need therefore, for a non-invasive low dose, sustained local delivery of myopia-suppressing drugs to the eye for the treatment of myopia progression. Such delivery should achieve maximal clinical efficacy while maintaining accommodation and pupillary function without extended periods of fixed or excessive dilation, rendering it an acceptable treatment to practitioners for its safety profile and to patients for its tolerability. Minimizing the dilation would protect the back of the eye from excessive UV light exposure over the years of treatment. Patients would experience reduced ocular side effects involving photophobia, inability to read, and inflammation of the ocular surface and lids, as well as various potential systemic side effects. A sustained delivery device worn on the eye also would offer the convenience of not having to take drops one or multiple times a day.

The present invention uniquely recognizes the importance of maintaining the dynamic function of the pupil and delivers the drug in a sustained manner, relying on a low rate of low variability delivery continuously over 24 hours a day, rather than simply reducing the concentration of a daily drop regimen. This constant, micro-dose delivery does not overwhelm or even affect the volume of the tear film during drug delivery, and maintains high treatment efficacy, while reducing attendant side effects from historical, experimentally effective drop concentrations that prove intolerable and impractical for clinical use. While the simple approach of a reduction in eye drop concentration has been shown to also reduce the efficacy of the treatment, the present invention aims to deliver drug at effective levels over the entire day and night, constantly driving it into the tissues at the back of the eye. Such constant, micro-dose delivery will not overload the receptors of the more anterior tissues at any one time and create undesirable side effects, but rather continuously deliver the drug to the internal eye to maintain adequate levels at the retina to continuously retard the progression of myopia.

Contact lenses have been proposed to deliver various drugs to duplicate the effects of drops, such as cycloplegia induced by atropine to treat myopia (U.S. Appl. 20140036225 to Chehab). But current contact lenses, and to our knowledge modified contact lens materials under development—none being currently available commercially—including those with the addition of liposomes, nanoparticles, molecular imprinting or incorporated films, all have stated goals of attaining clinical treatment comparable to current approved drops, and no case has been made for new treatment approaches involving ultra-low, in the range of micrograms or less per day, sustained dosing of current medications as is the case of the present invention. Furthermore, the overall shapes of contact lens designs are not favorable for extended periods of drug release as they are uniformly thin. The lenses consequently release drug too quickly, not having the bulk areas in their shape to enable long term drug diffusion and release at consistent very low doses.

The lenses consequently release drug too quickly, not having the bulk areas in their shape to enable long term drug diffusion and release at consistent very low doses.

In U.S. Appl. 20140036225 Chehab describes a contact lens with myopia control optics that also contains a muscarinic blocking agent. The incorporation of the muscarinic blocking agent into the contact lens is performed after the lens is manufactured by dissolving the agent in a solvent and placing the lens in that solvent for a period of time. The agent diffuses into the polymer matrix until equilibrium concentration is reached. The final concentration of agent in the lens is governed by the partition coefficient of the system. At that point the solvent is removed and the lens packaged, presumably in a drug solution to prevent elution during storage and shipment. Due to the limitations of such a system, the drug comes out fairly quickly once the lens is placed on the eye, and it is stated in that application that 80% loss is expected, so that the amount delivered from the device is measured as milligrams per day.

Contact lens delivery systems are intuitively appealing, and hence have been proposed for decades, and activity continues on those efforts. But conventional contact lenses cannot deliver drug for very long and there are several disadvantages to delivering a drug using a contact lens. The dimensions of the lens, choice of material and material chemistry available in contact lenses are all quite limiting. This is due to the restrictive necessities of covering the pupil but remaining very thin for comfort, having substantial proportional material and water phases, being optically clear and finished, and being highly oxygen permeable. As a result, a limited amount of drug can be incorporated into a conventional contact lens (typically only the water phase), and it all comes out of the lens very quickly, as it is all near a surface to start with. The basic lens material chemistry cannot be specifically tailored to any useful degree to the chemistry of the drug in order to optimize solubility, uptake and release kinetics without adulterating the necessary oxygen permeability and optical qualities. Oxygen permeability is a critical property of any device that will cover the cornea for any substantial proportion of the day or night. Without it the cornea cannot function and becomes more vulnerable to invasive blood vessels and blinding infections. Optical quality and clarity are necessary for the wearer to be able to see through the device. Any material or structural modifications to overcome these limitations of oxygen permeability and optical quality very quickly result in an extensively engineered and expensive contact lens, possibly rendered unwearable by most people, and/or unwearable on any extended wear (overnight) basis, for drug delivery. In spite of sophisticated modifications much of the drug, 40-90%, comes out in the first one to three days. Therefore, such as system could not work for myopia control progression with a drug such as atropine. Loading adequate drug to deliver a sustained dose over several days, weeks or months that would adequately control myopia progression would lead to a relatively large initial burst. As a result, too much drug would come out initially, leading to an excessively dilated pupil for several days, even after the level of release had decreased. This would be more akin to the peak/trough eye drop delivery, but once every few days instead of daily, than to a narrowly controlled range of sustained, low dose delivery for weeks or months. Mitigating this initial burst would require a preconditioning step of a few days in buffer to elute out the unwanted initial burst of drug, as suggested by prior art literature. Such a procedure would have regulatory and practical complications, as it could be difficult to coincide with the patient's dispensing visit and would have to be done using a sterile procedure or in a solution with substantial preservatives or disinfection agents that would minimize microbial growth.

It should be noted that most people are not able to sleep in contact lenses even when the lenses are designed optimally for such use, irrespective of any additional material or engineering requirements introduced for drug delivery. In fact, a significant portion of the population of successful daily wear contact lens wear patients are not able to wear their contact lenses even all waking hours every day, for a variety of reasons related to activities, environment, dryness and discomfort. That is one of the reasons there are so many different lens materials, with varying moduli and comfort sensations. Daily removal of drug-releasing lenses requires cleaning, rinsing and overnight disinfecting solutions, and would result in variable drug loss due to the drug release into the solutions. Daily disposable lenses would have to be packaged, or potentially rehydrated, in solutions that would also have to be modified to prevent drug loss from the lens. These solution requirements complicate the care and storage regimen and the regulatory approval, and increase development costs and expense of the use of the end product. And of course, if various polymers were produced to increase the number of comfortable wearers, each drug delivery material would require separate regulatory approval.

Due to the challenges of incorporating drug into a contact lens type device for sustained delivery, various other topical devices and implants have been developed for sustained drug delivery to the eye. Similar to the contact lens approach, that is to say, taking a device that has a history of being tolerated in the eye by a reasonable proportion of patients, punctual plugs, originally used to treat dry eye by blocking or partially blocking the drainage of the liquid tears from the eye, have been the subject of attempts to adapt them to drug delivery. Loading drug into various materials that are configured to fit into the tear drainage tissue openings has led to some limited clinical trial success but no marketed products to date. Their most significant limitations are issues with accidental and potentially undetected ejection, excessive tears, canaliculitis, and difficulties loading enough drug into these necessarily tiny devices to achieve clinically effective drug release over time, as they must be replaced when they run out of drug, requiring a visit to the doctor's office.

Other approaches to sustained delivery devices involve those with sizes and shapes predicated on the art of tablet manufacture and the desire to be inconspicuous in situ. That is, comfort and retention in the conjunctival sac is attained by slipping a device of simple manufacture, and usually of unspecified material, into the pocket formed by the conjunctiva lining the eyeball and the inside of the eyelid, and presuming it would be tolerated by the subject by virtue of its small size. This lack of design specific to the limiting contours of the intended space leads to discomfort and too-frequent ejection of devices of any significant volume, and few of these devices were developed as far as clinical investigation. This limitation of overall dimensions in turn again significantly restricts the amount of drug they are able to contain and consequently deliver. Nevertheless, efforts continue in this field in response to the recognized need. An example of a device large enough to carry substantial drug for sustained release, yet has dimensions to fit comfortably and with stability in that conjunctival sac, is Leahy et al, 2012.

An example of a commercially produced ocular insert for sustained drug delivery is found in the subject of U.S. Pat. No. 3,618,604, the Ocusert®, assigned to Alza Corporation. This product was designed from an engineering standpoint of making a drug-releasing "sandwich". Adequate retention and comfort were presumed by virtue of its small size. Several subsequent patents assigned to Alza Corporation (U.S. Pat. Nos. 3,416,530, 3,828,777) also describe devices that are designed to improve drug delivery kinetics based primarily on material characteristics. These patents utilize a simple design for devices that are "adapted for insertion in the cul-de-sac of the conjunctiva between the sclera of the eyeball and the lower lid, to be held in place against the eyeball by the pressure of the lid". This prior art is an example of using sustained release from their material chemistry to replace eye drop therapy, in order to minimize the effects focusing ability while maintain the drugs desired clinical effect inside the eye, which happened to be intraocular pressure reduction. The drug they used, pilocarpine, was marketed for treatment of glaucoma under the tradename, Ocusert®. Ocusert® had practical advantages (similar to the proposed device herein) of delivering a continuous low-concentration topical dose, in order to reduce side effects, while maintaining efficacy; when compared to pilocarpine topical drops, in that it demonstrated reduced drug side effects, such as excessive focusing and pupil constriction. (Note, however, that these side effects are the opposite from the side effects of anti-muscarinic drugs, which our device is designed to reduce or eliminate). Ocusert® was able to deliver a continuous effective dose for a week or two, with a single administration. However, significant problems in retention and irritation with the use of the Ocusert® devices are reported in the literature. In fact, for those reasons and because pilocarpine is now lower on the list of preferred pressure lowering agents, the products have been discontinued.

An important teaching from this prior art is that it demonstrates, at least for a couple of weeks, that a device can deliver a low dose to the surface of the eye in a sustained manner and maintain efficacy, while substantially reducing undesirable pupil and focusing side effects that is typically seen with the corresponding eye drop administration. Such delivery exceeds the capabilities of even state-of-the-art repeated daily eye drop therapy. The subject invention, herein, also reduces pupil and focusing side effects (opposite to those of pilocarpine reduced by the Ocusert®'s delivery) while maintaining a desired clinical effect, but presents a more sophisticated matrix that can deliver a tighter range of drug release over the course of treatment, and for more than twice the treatment time of that prior art. And, in addition, this device can shaped to the surface of the sclera, so that the retention and irritation problems, as seen with the use of the Ocusert® device, are eliminated.

The prior art on noninvasive ocular device drug delivery, whether through the adaptation of contact lenses or punctual plug devices, or through devices developed de novo specifically for drug delivery, thus teaches attempts to present drug at the front of the eye for sustained release, in order to mimic and improve upon the recognized clinical treatment effects of, and replace the use of, currently available eye drops, for their current disease treatment applications. Many of these device patents and applications are proposed as platform technologies, claiming sustained release of a wide range of potential candidate drugs based on their historical use in eye drop treatment regimens. They seek the same clinical treatment effects, while perhaps reducing known side effects somewhat. They do not, however, specify a material chemistry and device that would deliver these drugs in a way to provide any specific therapy option not available with drops.

More specifically, the prior art, for topical ocular drug delivery devices does not teach ways to design a device with a polymer matrix that will continuously deliver drug to the surface of the eye, at a sufficient concentration to transport drug to receptors in posterior ocular tissues, while presenting a low enough concentration (a "micro dose") anteriorly, to minimize undesirable side effects triggered by receptors in anterior tissues. The art recognizes that attempting to get drug deeper into the eye with eye drops briefly and necessarily overwhelms the front of the eye with drug in order to drive drug into the eye, causing side effects. Immediately subsequent to that, when the drop has washed out of the tear film after a few minutes, there is little remaining impetus to continue to drive drug diffusion further into the eye. The art has focused, rather, on trying to get enough drug into the eye to the same target tissues as the drops, simply to mimic or enhance the same mechanism of action and treatment efficacy of the drug in eye drops, while avoiding the necessity of applying the eye drops.

Not everyone's pupil is the same size in the same light conditions, and everyone's pupils normally change size according to ambient light conditions, constricting in brighter conditions and dilating in darker conditions, working much like a camera's aperture. But no one is comfortable with an excessively dilated or fixed, dilated pupil. The pupil must be able to constrict to increased light and dilate in response to a decreased ambient light level. That is its function and it must be maintained for patient comfort and vision in various light levels. It needs the ability to have a relative size change under changing light conditions in order for the individual to be comfortable. The absolute size is a factor but not the critical factor. A group of people together in a given ambient light level environment can have a variety of different pupil sizes (within limits) and yet all be quite comfortable. It is the ability to change size in changing light that must be maintained.

The retina needs to function effectively over an extremely large range of sensitivity. The range from dark threshold to a light level that can possibly cause damage covers a luminance range of about 14 log units. This is a range of 1:100,000,000,000,000. At the lower end of this range the visual system trades color perception and good visual acuity for very high sensitivity to low light levels. The eyes take time to adjust to different light levels, and the dynamic range of the human eye in a given scene can actually be quite limited due to optical glare. The pupil plays a critical role in regulating and adjusting to light levels that reach the retina by giving it a chance to adapt to changing levels as well as regulating the total amount of light reaching the retina at a given time. This is especially true at the ranges where proportional response of the rod and cone photoreceptors change, on either end of the mesopic range. For example, in slightly brighter conditions than that, as the photopic range is entered, rod saturation begins and the rods output no longer increases as luminance increases. They are already responding as vigorously as they can. A pupil that can constrict normally on increased light helps the retina respond more comfortably to this increased brightness. And of course when the total light and its energy is high enough, such as in the case of an excessively dilated pupil it can cause retinal damage. The lower dose atropine drop studies reported that the children easily tolerated 1 mm larger pupils than they normally have under normal light conditions, with very few (6%) in that study group (vs.>60% in the higher dose groups) asking for tinted glasses, demonstrating that an increased pupil size vs. an individual's "normal" size is well tolerated, as long as it is not too excessive. The normal drop dose studies demonstrated that a very large, fixed pupil is not tolerated well at all. Nor is it considered safe over the long term, due to the likely excessive exposure to UV light to the internal eye. The lower doses also did not cause the children to be unable to read as occurred with the standard drops. In fact, despite some mild glare symptoms in a study with 0.01% drops, there was no decrease in visual acuity, quality of life or reading speed. And of course routine eye exams demonstrate that even an hour or two of excessively large and unresponsive pupils and inhibited focusing is disliked by most patients who must try to function normally, such as driving or working, after they leave the appointment.

To counteract the growing hours of intense near focus during the day, including studying and what is often referred to as "screen time", it is recognized in the field that the proposed optical treatments described above would be expected to be more effective if they are extended throughout the waking hours. And in the case of a pharmaceutical potentially affecting the continuing growth of the eye, it is recognized that it would be preferred to provide a sustained release system to deliver small amounts of drug steadily over the course of the day and night. It is also recognized in the field that the drug cannot interfere substantially with the ability of the patient to perform those very same intense near focusing activities, either by the ocular side effects of fixed and dilated or excessively dilated pupils, or by limiting the ability to focus up close (cycloplegia). Such side effects have been demonstrated to be intolerable and cause drop out from the treatment regiments with the 1.0% atropine drops, for example. Additionally, it would be unacceptable to expose the eye to excessive ultraviolet light rays through a fully dilated pupil all day, over several years of treatment of the myopia, only to expect an increased complications of retinal toxicity, early cataract and macular degeneration later in life.

With atropine and other anti-muscarinic agents, the maximally dilated pupil and inability to constrict in increased levels of ambient light is achieved with standard atropine eye drop dosing, which historically have been used for purposeful complete dilation for ocular examination or for acute, not longstanding, treatments of inflammation. Consequently, such treatment is associated with the expected, unacceptable levels of light sensitivity, increased UV exposure and visual blur for several days, often after a single drop of historical and current clinical eye drop doses.

Despite these side effects, conventional clinical atropine eye drops, in the available doses of 1.0% and at times 0.5%, have been tried for the treatment of myopia progression. The driving thought for this approach was originally intending to affect pharmacologically the same mechanism of action as one of the primary mechanisms of action of the clinical drop dosing, that of cycloplegia, or paralyzing the accommodation, or near focusing ability, of the eye, which had long been proposed, and expressed as "excessive near work", by scientists and clinicians in the field, as a primary cause of increasing myopia. This line of thought came out of the common observation that patients that tend to perform excessive near work tend to get more nearsighted over time when continuing such near tasks, such as young Jewish men studying the Torah for hours a day, people getting jobs in data entry or other intense computer-use occupations, returning to hours of studying in professional school, etc. While eye doctors could track individual patients thus affected, not all patients are thus affected and proving the effect in large controlled studies has been obfuscated by the disproportionately large influence of genetics. Nevertheless, it remains common perception that excessive near work causes increased or perhaps even the onset of myopia (perhaps in those so predisposed genetically), and the increasing worldwide prevalence of myopia with increased near vision demands associated with increasing urbanization and education, trending to 80-90% of Asian youth today, and 50% of the world's population by 2050, lends credence to what has been apparent to lay and professional observers. This phenomenon is often expressed as the unproven maxim that the more you wear your glasses for myopia correction (glasses for myopia increase the accommodative demand more than not wearing them) and the more near work you do, the more nearsighted you will get. However, subsequent to and in addition to that intuitive proposed mechanism of action, it was shown that anti-muscarinic agents, independent of their effects on pupil dilation and focusing, have the desired effect of reducing the growth of the eyeball as measured by increasing axial length in progressive myopia. These effects take place further back in the eye, likely at the dopamine receptors of the retina. And eye drops do not deliver drug to the retina effectively, especially when their concentration must be reduced to avoid the side effects on the pupil and focusing that occur more toward the front of the eye where the drops are applied. Currently approved myopia treatment does not exist, but the off-label use of low concentration drops, such as 0.1% or 0.01% is occurring more in certain countries, reflecting the recognized need to address this growing problem with an effective and practical treatment.

SUMMARY

The present invention is directed, at least in one embodiment, to a non-degradable topical ocular device, shaped to adhere to a non-corneal surface of the sclera, with a matrix designed to provide continuous drug delivery of a muscarinic blocking agent and/or a dopamine agonist to the eye, at sustained low-dose drug concentration(s) that can moderate the progression of myopia, while minimizing local and systemic adverse effects.

The matrix of this device is specifically designed to incorporate the drug(s) via complexation of a drug's basic nitrogen with an organic acidic monomer during polymerization of an ophthalmic device. As a consequence of polymerization, the acid moiety becomes fixed while the complexed drug is mobile. In this manner, the drug is released from the device in a sustained fashion in microdoses over weeks or months, to effectively slow or stop myopia progression.

Thus, in the practice of the present invention herein, the agent is dissolved in the formulation composition prior to polymerization into the ocular device geometry. This method of creating the ocular device allows a more controllable agent concentration in the device matrix, which is especially important when preparing the low dosage devices of this invention. It also allows a more sustained, lower dose release rate. The release rate can be orders of magnitude lower than that of a contact lens delivery system such as that of Chehab, and spread out over the entire 24 hr day, reaching as low as fractions of a microgram per 24 hours, whereas the contact lens would most likely be removed in the evening for the night, after releasing a much higher dose over about half the time.

Atropine is a naturally occurring tropane alkaloid and is classified as a non-selective anti-muscarinic agent that works by blocking muscarinic receptors that are found in the muscles of the eye and which are involved in controlling the size of the pupil and the shape of the lens. Its common clinical use has been very short term therapy to cause fixed dilation of the pupil for eye examination or treatment of acute inflammation. Additionally, it has been demonstrated in studies of long-term ocular instillation to be useful for the treatment of myopia. However, ocular instillation of atropine via eye drops results in variable delivery of the drug at high, sporadic doses, with no drug delivered to the eye between eye drop dosing times. This results in unacceptable vision, light sensitivity and other ocular side effects in most cases, as well as delivery to the systemic circulation and risk of associated adverse effects such as tachycardia, elevated body temperature and agitation. There is also a significant rebound effect in myopia progression upon cessation of treatment, perhaps from hypersensitivity of the receptors. As a result of these side effects, long-term compliance with atropine therapy for myopia is poor. Lower concentration doses administered by eye drops greatly improve the side effect occurrence and severity, but are not as therapeutically effective. The rebound effect on cessation of treatment, however, is also lower. Accordingly, there is a need in the field for delivery of a selective or nonselective muscarinic antagonist via a device that is in contact with the eye most of the time, does not require frequently removal and replacement, and by its material characteristics and dimensional aspects can deliver the drug at very low doses in a sustained fashion, thereby maintaining a near-normal steady-state functional ability for pupil dilation and constriction and near/far focusing ability.

The drug-loaded device, described herein, delivers drug in a manner unachievable with the pulse dosing of drops. It provides a continuous sustained-release micro-dose of active drug, targeting putative receptors in the retina and potentially acting on the lens of the eye. In doing so, the objective of this invention is to provide effective treatment of myopia while minimizing adverse effects (e.g., compromise of the pupillary function and focusing ability of the eye). Furthermore, since the device of this invention can be placed under the eyelid, away from the cornea, the patient could continue to benefit simultaneously from any refractive correction of myopia utilized independently of this invention, at their convenience, such as eyeglasses, contact lenses, or refractive surgery. Virtually all myopia patients could therefore benefit from the use of this invention, and compliance with myopia treatment would be improved over other proposed options that are applicable to a more limited myopia patient population, such as drug delivery devices that would cover the pupil (a contact lens-based device), or repeated daily topical instillations of a pharmacological agent, such as atropine, in an eye drop delivery system.

The matrix compositions described herein are combined with the features of the device disclosed in U.S. Pat. No. 8,167,855 B2, issued May 1, 2012, which is hereby incorporated by reference in its entirety, to provide a novel device that can be used to slow, retard or prevent myopia progression while minimizing local and systemic adverse effects

BRIEF DESCRIPTION OF THE DRAWING FIGURES

Certain preferred embodiments and modifications thereof will become apparent to those skilled in the art from the detailed description herein having reference to the figures that follow, of which:

Figure 6:
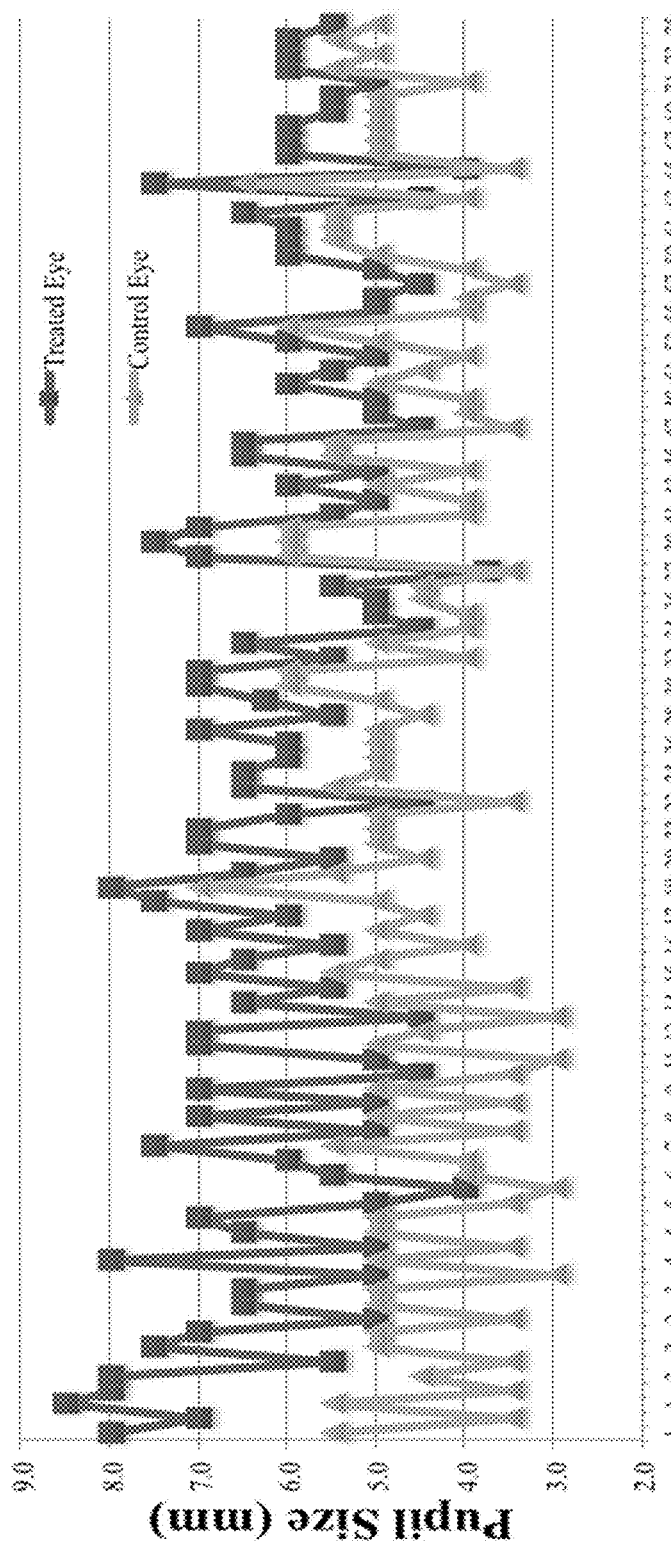
Figure 7:
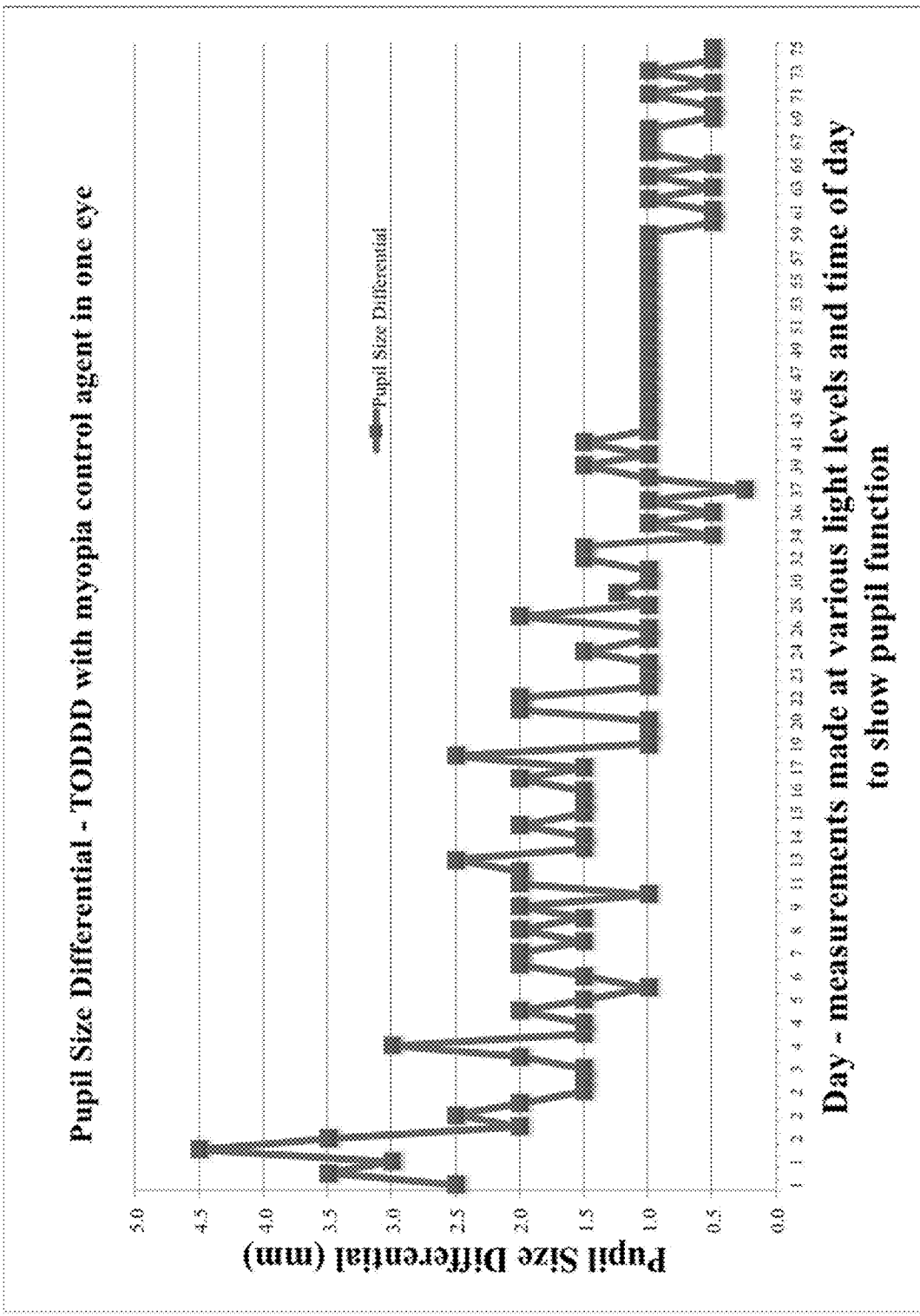

FIG. 6 is a plot of pupil sizes of treated eye vs. control eye, for device releasing micro-dose of atropine, demonstrating immediate but not persistently excessive relative pupillary dilation of treated eye, and ongoing pupil function; and FIG. 7 is a plot of pupil size differential between the treated and control eyes, for device releasing micro-dose of atropine, demonstrating acceptable and persistent relative difference in pupil size throughout the treatment period following a single insertion of a device.

DETAILED DESCRIPTION OF CERTAIN EMBODIMENTS

Although atropine, atropine sulphate monohydrate and pirenzepine are described herein, other anti-muscarinic agents can be used, such as, racanisodamine, cyclopentolate, homatropine, scopolamine, telenzepine, nuvenzepine and rispenzepine. In addition, other classes of drugs or therapeutic agents may also be utilized in accordance with the present invention, for example, dopamine agonists, including apomorphine, bromocriptine, quinpirole, levodopa and adenosine agonists such as adenosine, 7-methylxanthine, ATL-146e, 2-(1-octynyl)adenosine, CGS-21680, DPMA, regadenoson, UK-432,097, Limonene and 5'-(N-Ethylcarboxamido)adenosine (NECA).

The anti-muscarinic agent in the present invention would not have to be "loaded" into a finished device, such as a contact lens, or reloaded between daily wearing and disinfection of contact lenses, as described in EP 2 693 259 A1 to Chehab et al. Such a contact lens-based delivery system would necessitate the evolution of a cleaning, disinfection and storage regimen into a cleaning, disinfection and storage regimen that also involves a concentrated drug solution, or, alternatively, the addition of a second, separate drug loading solution to the daily contact lens regimen. Patient compliance and adequate ability to follow instructions handling an additional, drug-laden product present substantial challenges to development and adoption of such a system.

A further disadvantage of loading drug in such a manner into a conventional hydrogel contact lens results in a relationship between the active drug and the contact lens material that leads to a relatively short duration of a rapidly declining rate of release—with depletion within hours to a day or so. Much of this is due to the uniformly thin nature of the contact lens shape with its very high surface to volume relationship that results in all of the drug being close to its surfaces, leading to a rapidly dissipating release. The drug must be soluble in the water phase to be in a solution to load into the lens initially, so it will tend to quickly diffuse through the water phase and out of the lens, into the physiological environment surrounding the lens. A low-dose release, at effective levels, over time has not been demonstrated with a contact lens-based delivery system. For example, a conventional contact lens of approximately 50% water made in a Polyhydroxethylmethacrylate [pHEMA] based hydrogel, soaked in a solution of a drug salt to load it, would primarily contain drug only in the water phase as favored by its partition coefficient. Simply increasing the loading concentration of the lens would not necessarily substantially extend a delivery of a low dose of drug, as the mobility in this phase would be expected to be quite high and the increased drug load would simply be expected to come out at a higher rate.

For example, by manufacturing the composition of the subject invention disclosed herein, in a device designed per the teaching of Leahy et al, US patent, U.S. Pat. No. 8,167,855 B2, issued May 1, 2012, the lobes disclosed in the Leahy et al patent should have an adequate thickness in this material to contain and subsequently release enough drug at the sustained, low-dose rate to effect a reduction in the progression of myopia, while at the same time, over the course of treatment, maintaining a functioning, reactive pupil and near/far focusing ability. It is envisioned that such sustained, steady, low-dose delivery would avoid the ocular and systemic side effects that are experienced with drop treatment using the same drugs.

Figure 1B:
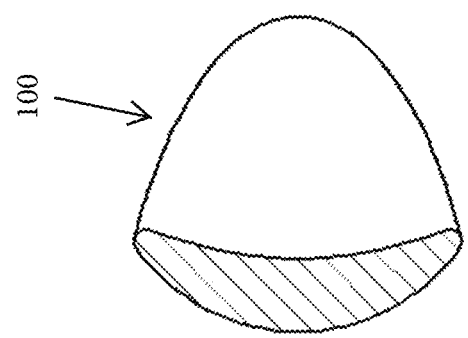
FIG. 1B is a cross-sectional view taken along the line A-A of FIG. 1A.
Figures 1A, 1C:
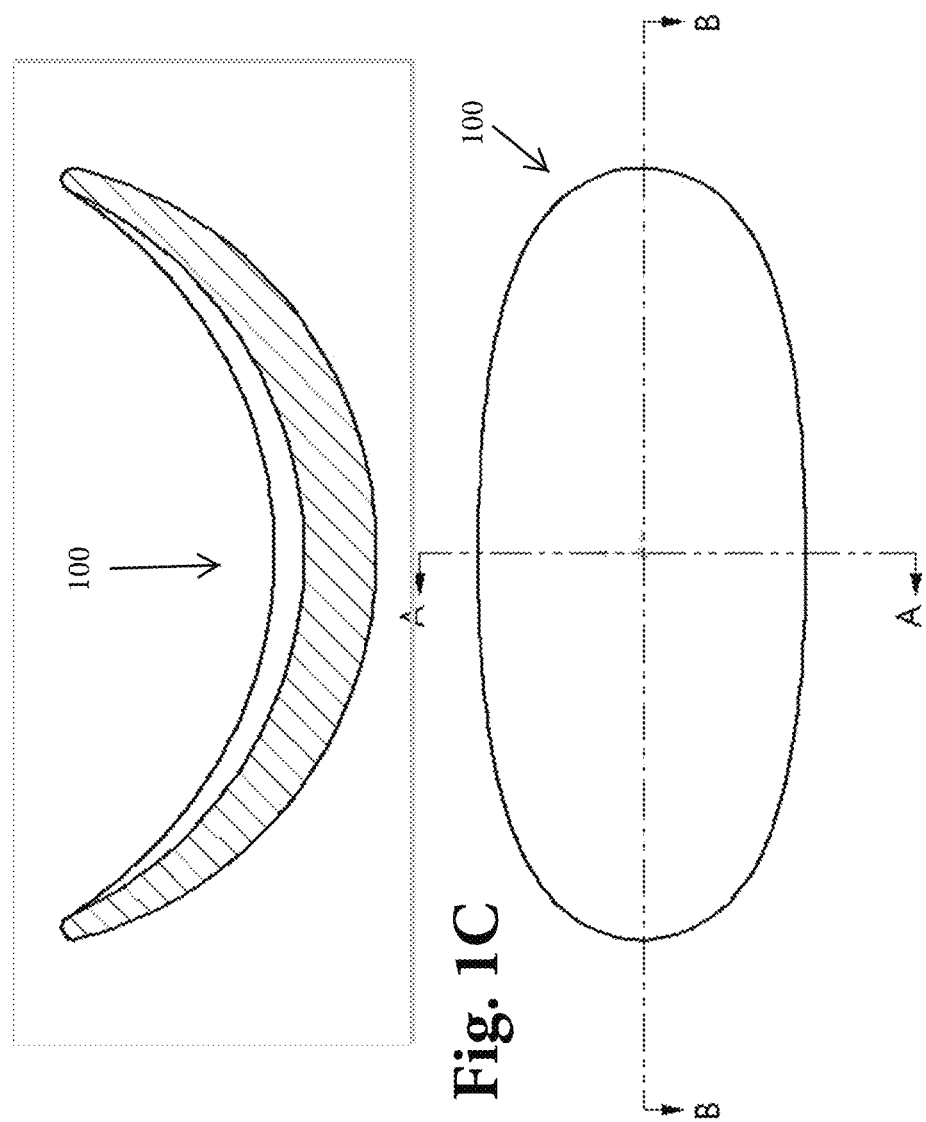
FIG. 1A is a top plan view of an ocular drug delivery device according to a first embodiment.
FIG. 1C is a cross-sectional view taken along the line B-B of FIG. 1A.
Figure 2C:
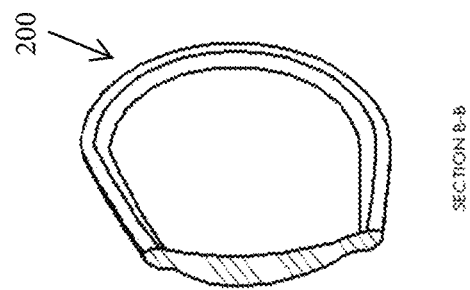
FIG. 2C is a cross-sectional view taken along the line B-B of FIG. 2A.
Figure 2B:
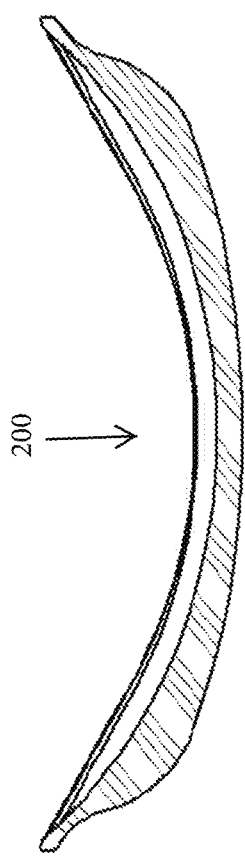
FIG. 2B is a cross-sectional view taken along the line A-A of FIG. 2A.
Figure 2A:
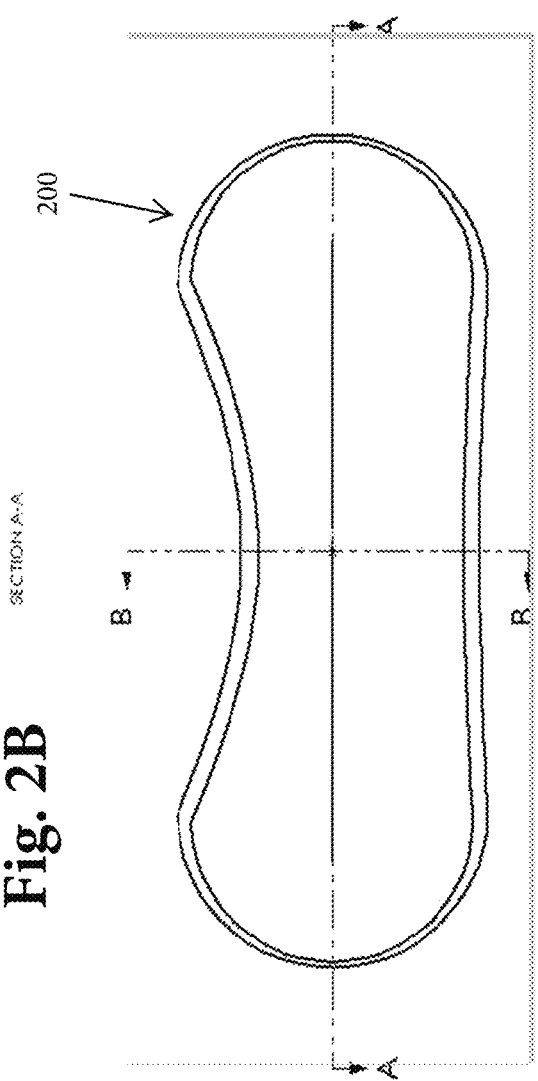
FIG. 2A is a top plan view of an ocular drug delivery device according to a second embodiment.
Figure 3:
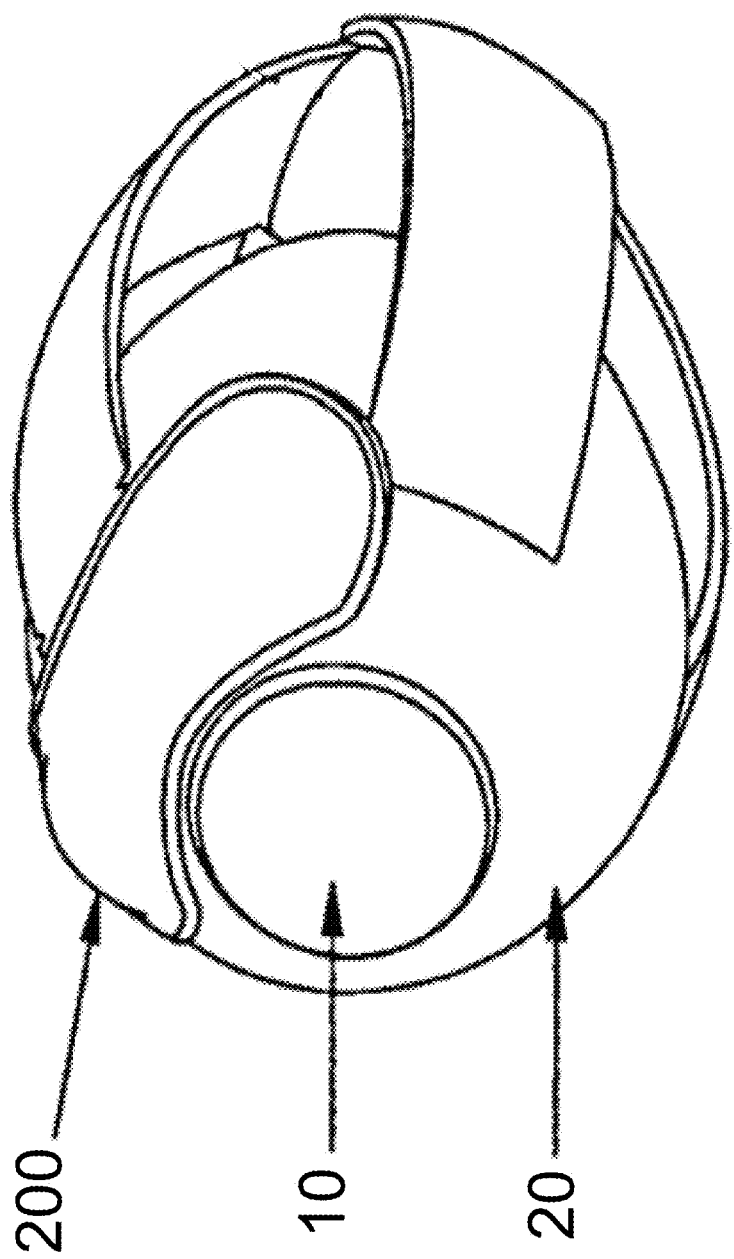
FIG. 3 is a perspective view of an eye with the device of FIG. 2 fitted to the superior sclera of the eye.

FIGS. 1A-C and 2A-C illustrate exemplary shapes for an ocular drug delivery device made in accordance with the present invention. More specifically, FIGS. 1A-C illustrate an ocular drug delivery device 100 and FIGS. 2A-C illustrate an ocular drug delivery device 200. These constructions are described in more detail in applicant's previous patents that are referenced herein. FIG. 3 is a perspective view of an eye with the device 200 of FIG. 2 fitted to the superior sclera 20 of the eye and being spaced from the cornea 10.

Using an appropriate device design, as produced in Example 4 herein, allows the device to be worn on the eye continuously, and as found in Example 7, should deliver drug in a sustained fashion for weeks or even months. It is envisioned that continuous wear of a device providing sustained, constant micro-dose delivery would minimize side effects and deliver effective myopia progression treatment at all times, thereby counteracting the constant stimulus to further progression that is experienced throughout the day from normal, modern-day visual activities.

The preparation of two such devices with 0.5 and 0.05% w/w atropine, respectively, is described in Example 7. The device with 0.05% atropine was tested in a clinical study [Example 7] and found to maintain reactive pupils and near focusing function throughout the two-months of wear. Several milligrams of drug, at a few percent by weight of the entire device, and ranging down to about a hundredth of a percent by weight, could easily be incorporated into the device in the material composition of the subject invention. Such material composition, in contrast to a drug-loaded water phase of a soft contact lens hydrogel material, allows for slow diffusion of micro-doses of the complexed active agent out of the matrix to the surface of the eye, at a more uniform rate and for a sustained period of weeks or months. This micro-dose delivery profile should provide adequate drug to the tissues in the eye to decrease myopia progression, without periodically overloading the tear film as does an eye drop during delivery.

In the case of an embodiment of the subject of this invention incorporating and delivering a dopamine or adenosine agonist from an ophthalmic device, for the purpose of inhibiting the abnormal postnatal axial growth of the eye, it is desirable to maximize the delivery of the therapeutic agent to the vitreous humor and retina, while minimizing systemic absorption of the agent to prevent possible systemic side effects.

Delivery of a therapeutic agent to the posterior ocular chamber is challenging because there are multiple static barriers for the drug to penetrate and, multiple dynamic barriers that may rapidly eliminate the drug. Also, there are efflux pumps that pose a significant challenge for drug delivery. To one skilled in the art, one approach to overcome these barriers might be to apply a high-concentration topical ocular solution. However, since the majority of the topically applied dose will exit through the nasolacrimal canal, systemic adsorption could lead to serious adverse effects, particularly with dopaminergic and adenosine agonists. Another approach may be to prolong the residence time of a therapeutic agent by increasing the formulation viscosity or by employing a mucoadhesive formulation.

Alternatively, formulation changes that increase membrane permeability and/or enhance non-corneal drug access may also be a way to maximize the ratio of ocular to systemic drug absorption. For example, adding 3.75% poly (vinyl alcohol) into an ophthalmic formulation afforded a 52-fold increase in the iris-ciliary body to plasma drug concentration ratio.

Another approach to improving ocular absorption of a drug is to add a penetration enhancer to the formulation. However, most of the penetration enhancers may also damage the cornea.

One skilled in the art may improve selection by choosing the most appropriate dopaminergic or adenosine agonist from the standpoint of optimal physical-chemical characteristics to favor local ocular absorption [e.g., log partition coefficient around 2-3].

The above approaches, by no means, cover all the methods available, to one skilled in the art, to improve topical drug penetration. But, suffice to say that getting sufficient drug to posterior tissue, without significant local and systemic adverse effects is a major challenge.

In addition to the above challenges, the instability of most dopamine agonists make it difficult to formulate a stable solution. To be commercially viable, a formulation must be stable (i.e. NMT 10% loss of active for at least 18 months). Typically, to stabilize a dopamine solution, a low pH in the range of 3.5-4.5 is required. But, this pH range, in addition to stinging, may damage ocular tissue and/or, precipitate at physiological pH. In contrast to solution instability, dopamine agonists are anticipated to be far more stable in the solid state and hence, the device described herein should provide significantly improved environment for the stability of dopamine agonists.

As a consequence of eye drop solution challenges, no commercial formulation containing a dopamine agonist has thus far been developed that is stable, safe and effective for treatment of myopia progression. An attempt to get around this problem with cyclodextrin formulations only showed stability for 30 days.

Another approach to addressing the problem of delivering dopaminergic drugs, is by soaking a contact lens in a drug solution prior to insertion. A conventional commercially available contact lens product, made of a hydrogel material such as etafilcon A or a silicon hydrogel such as narafilcon A or B, galyfilcon A or senofilcon A, regardless of its potentially useful optical design, would have many technical, engineering and cost hurdles to overcome, not only in its drug loading manufacturing steps, but also in product storage, drug release kinetics and many wearing and compliance challenges in the hands of the young patients.

Despite many decades of trying to deliver drugs from conventional or variously modified contact lenses, success has not been achieved to a widespread practical and useful degree. Even if such a lens could be reasonably fabricated, the number of patients that would be able to wear such devices successfully and effectively would be substantially limited. A myopia-suppressing drug (e.g., atropine) is highly unlikely to be released from commercially available contact lens materials in a manner controlled enough over time to achieve efficacy in treating myopia progression while maintaining pupil reactivity and ability to see reading materials and computer screens. As a result, such lenses would not be well tolerated by patients, nor would they be prescribed by doctors wary of the potential retinal toxicity, cataract formation and macular degeneration resulting from repeatedly and excessively dilated pupils. Not everyone's pupil is the same size, but no one is comfortable with an excessively dilated or fixed, abnormally large pupil for that individual. The pupil must be able to constrict to increased light and dilate in response to a decreased ambient light level.

Incorporation of a dopamine agonist into a solid material as the subject of this invention should mitigate any stability and solubility problems inherent in formulating an ophthalmic solution for topical application to the eye.

Furthermore by complexing the drug in its formulation and polymerization, the use of the material of the subject of this invention also eliminates many subsequent problems inherent in trying to deliver drugs from a contact lens loaded with drug from solution.

In these preferred embodiments of the present invention, the myopia-suppressing drug-loaded device using the design of Leahy et al, 2012 would not interfere with the patient's current standard eyeglass and contact lens correction modalities. Children and young adults, the population most at risk for myopia progression, could continue to wear their customary, preferred glasses or contact lenses, with no impact from the addition of their myopia progression treatment on their normal activities and quality of life. Compliance would be enhanced by a child not having to choose between wearing glasses and contact lenses of their choice and pursuing activities of their choice vs. complying with their myopia treatment program. By avoiding repeated or constantly excessively dilated pupils, doctors would not have to balance the benefit of treatment against substantial risks associated with excessive UV exposure to the back of the eye. The advantages that result from the unique micro-dose, steady-state sustained delivery from such a device incorporating the subject of this invention would further encourage the adoption of such myopia treatment by doctors and patients alike.

The present invention, in a first aspect, provides a polymeric ocular device matrix material adapted for the tightly controlled, low- or micro-dose, sustained release of an anti-muscarinic agent upon application at the surface of the eye, said device being retained near or on the surface of the eye. Furthermore, said polymeric devices are capable of continuously delivering a myopia-suppressing drug, in a sustained low concentration, which is not achievable with the peak-trough nature of periodic eye drop delivery. The present applicant envisions that the device would be effective at suppressing the progression of myopia, while maintaining functional pupil constriction and dilation, and reading ability, throughout the treatment period. Such controlled therapy contrasts with the widely varying rate of drug delivery from eye drops of any concentration, which by its nature varies from maximal, typically excessive, drug delivery level at the time of drop instillation (since only 5% is expected to actually penetrate into the eye during the short residence time on the eye) to the zero drug delivery level for most of the time between drop applications. Constant diffusion of micro-doses from a polymer matrix offers a continuous low level of drug to steadily penetrate the eye, achieving therapeutic efficacy while minimizing the side effects of lingering excessively dilated pupil and focusing inhibition experienced with each drop instillation. Together with the reduced potential for ocular complications from excessive UV exposure through an excessively dilated and/or unresponsive pupil, the subject of this invention provides a far greater practical implementation and acceptance of anti-muscarinic treatment for myopia progression.

Incorporation of drug into applicant's drug delivery technology to date had involved the primary goal of adequate drug dosing to replace conventional current eye drop therapies for the active agents used. The level of drug delivery achieved was consistent with standard clinical drop treatment, or was considered to be ineffective due to inadequate drug release to mimic the recognized treatment effects of eye drop administration. That is, like other ocular drug delivery technologies, our initial approach had been that of trying to address the challenge of drug delivery to the eye by packing large amounts of drug into our matrix material, incorporating that matrix material in turn into as large a device as practical, thereby delivering enough drug to mimic current clinical eye drops effects, while maintaining sustainability of such recognized treatment effects. The goal of the invention of such an approach is to replace eye drop therapy in current clinical treatment protocols, while achieving the same, well-established clinical treatment effect over time. In the case of timolol this effect would be reduction of intraocular pressure in the treatment of glaucoma. In the case of atropine, the effects are short-term fixed dilation of the pupil and paralysis of the focusing ability of the eye. The claimed advantages of such inventions are decreased ocular and systemic side effects from the large short-term deluging of drug that occurs with eye drops, the lack of need for and absence of toxic preservatives, and improved compliance with sustained release devices over daily drop administration, rather than new treatments or disease applications of the drugs.

The history with topical and implantable ocular drug devices has been one of limitations of size and releasing material chemistry requisite to deliver enough drug to both achieve and maintain a clinical effect similar to current effective eye drop regimens. The best example of such an approach that has achieved some minimally acceptable results has been the punctal plugs, and various small topical inserts that last for days or weeks. It is recognized that larger matrix devices can deliver for longer periods of time but must be made in a device that can stay comfortably in the eye.

Figure 4:
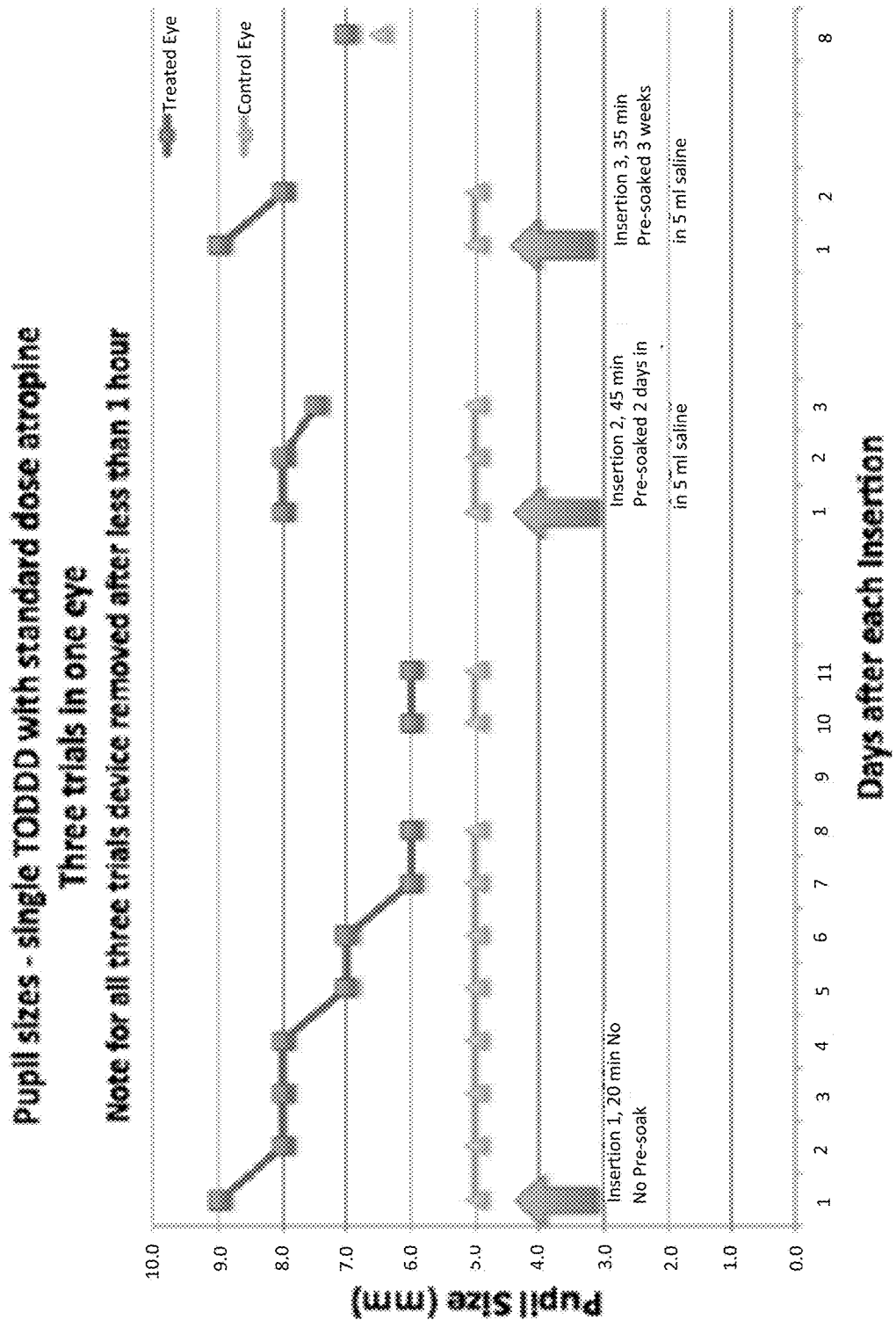
FIG. 4 is a plot of pupil sizes of treated eye and control eye, for device releasing standard dose of atropine, demonstrating immediate loss (and very slow recovery despite nearly immediate device removal) of pupil function in treated eye, similar to the effect of a clinical drop administration.

In applicant's experiments using this approach, applicant achieved adequate drug release result in the typical clinical effect of current eye drop administration, such as for an anti-glaucoma agent, for months. Applicant then formulated our material with atropine and achieved the same initial effects of atropine drops. This effect would be expected to continue as long as the device was left in, up to a period of months. That is, acute, fixed pupil dilation and paralyzed focusing ability. As shown in FIG. 4, simply pre-soaking the device in saline, to remove any initial burst, and subsequently soaking it again to remove even more drug, did not reduce these effects substantially upon insertion into the eye. This indicated to the present applicant the need for a device delivering a much lower dose of drug, but sustained over a long period, within a therapeutic window for myopia progression that would balance drug delivery with avoidance of the effects we get with conventional atropine drops. Doing so with the presently disclosed material in a devices of appropriate configurations would represent new treatment capabilities beyond the realm of currently available clinical drop administration, as well as an improvement over experimental "low-dose", such as 0.01%, clinical drop administrations.

Since atropine's effect on the dilation and focusing is achieved so quickly after administration of a drop, drop concentration dosing is limited by the immediate, maximal effect achieved. In the case of myopia progression treatment targeting the back of the eye with atropine, these immediate and lasting effects are considered side effects, not the desired treatment. Reducing the dose to decrease these side effects means that very little drug is effectively delivered to the desired site of activity for the remainder of the day between drop applications, thereby limiting the treatment effect on the myopia progression. The lowest dose eye drops studied, 0.01% vs. typical clinical drops of 1.0% or 0.5%, have been shown to have a less-than-optimal but measureable effect on myopia progression, but importantly were low enough to yield tolerable side effects for most patients and to be considered safe in studies of chronic treatment. A matrix device that could release drug on a 24/7 basis, while maintaining those low levels of side effects, would be expected to provide an improved myopia progression treatment, since more drug would penetrate to the target receptors towards the interior and back of the eye without overloading the receptors directly related to the undesirable side effects.

Figure 5:
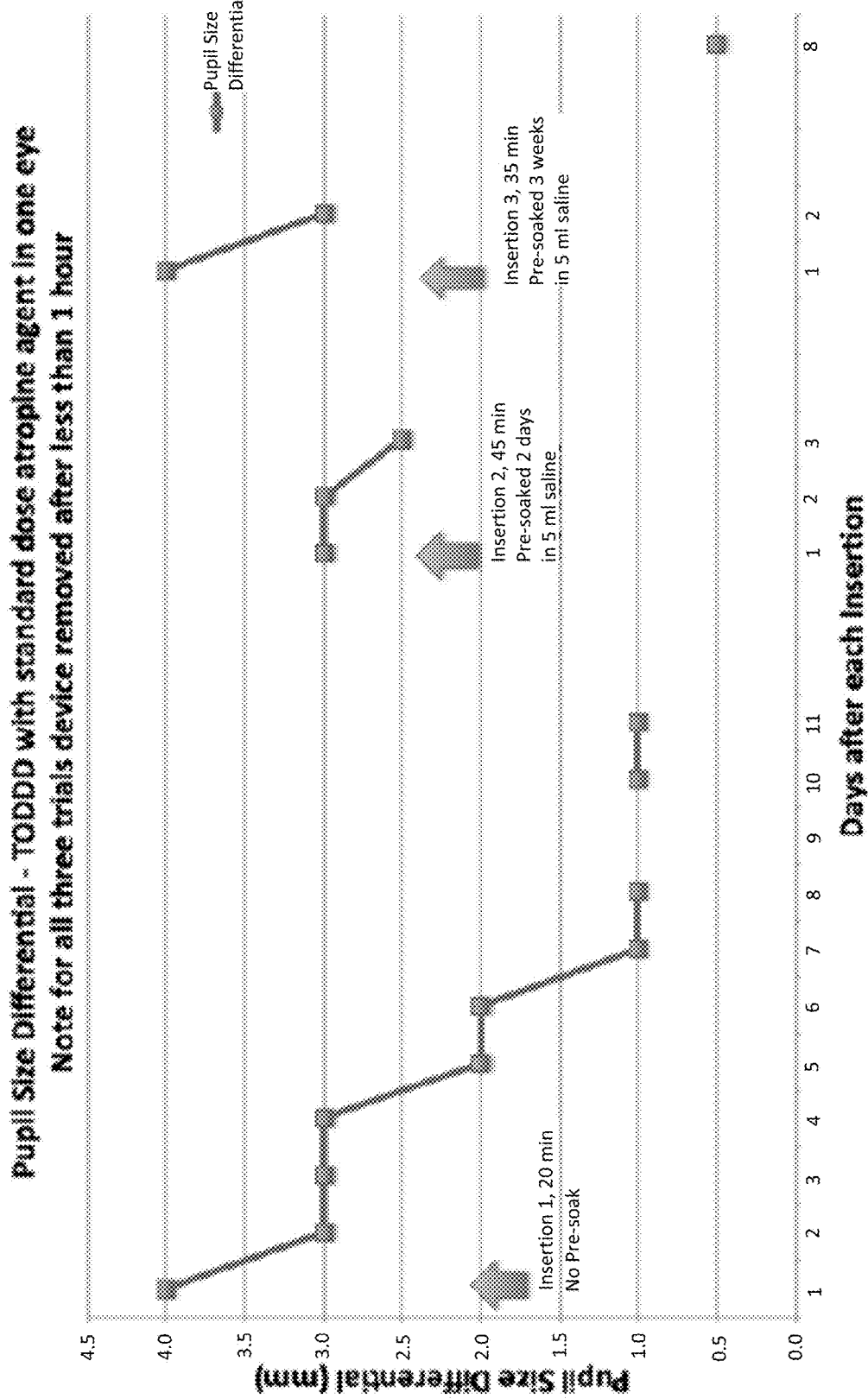
FIG. 5 is a plot of pupil size differential between the treated and control eyes, for device releasing standard clinically effective dose of atropine, demonstrating persistent excessive pupillary dilation of the treated eye following insertion, despite nearly immediate device removal.

Having established incorporation into the presently disclosed matrix chemistry of a dosing that released in the range yielding a result imitative of clinically established, useful drop concentrations, that is, for maximum, fixed pupil dilation and paralysis of accommodation, as shown in Example 5 and FIGS. 4 and 5, we proceeded to calculate bracketing amounts of drug loading to release from our matrix chemistry, in doses that would improve on the limitations of experimental low dose eye drop concentrations.

While for many decades the clinical use of atropine drops has been to establish short-term clinical effects of pupillary dilation and cycloplegia, the invention herein is designed to avoid, or minimize, such effects while providing long-term treatment for myopia progression. For the myopia progression treatment of this invention, we are using devices of this invention to deliver drug in a unique manner unachievable with pulse dosing of drops, using a controlled, micro-dose, continuous, sustained release device, targeting putative receptors in the retina and potentially acting on the lens of the eye. In doing so, we purposefully attempt to maximally preserve the pupillary function and accommodation, as we believe we do not need to substantially compromise the pupillary function or focusing ability of the eye in order to achieve an effective treatment.

The polymeric drug-loaded matrix materials of this invention can be molded into sophisticated designs for ocular devices, such as, of Leahy et al 2012, designed to fit the sclera of the eye so as to permit the device to be held on the eye by fluid attraction and be retained on the eye without aid of an eyelid.

The polymeric formulations useful in the practice of this invention are able to dissolve sufficient quantities of the anti-muscarinic agent in the range of 0.001 to about 5.0 weight percent. Following polymerization in a mold the shaped ocular device is formed and represents a "dissolved matrix" device and displays the release kinetics of such a system. Additionally, the device matrix properties are:
Glass transition temperature less than about 20° C.
Hydration less than about 2.0%
Crosslinked to provide structural stability
 In device forms large enough to contain enough drug to deliver drug via diffusion for extended periods
 In device forms thick enough in device sections to deliver drug via diffusion for extended periods
Biocompatible
Non erodible In accordance with the practice of presently disclosed ocular devices, it has now been unexpectedly found that certain polymeric materials can be used for forming devices for the controlled micro-dose release of a myopia-suppressing drug, for example atropine, clinical level of therapy unachievable with eye drop delivery. The use of and advantages realized by the disclosed polymeric materials are unexpected because they can be formulated to accept a useful range we have found that atropine, incorporated into a drug delivery device using these materials, can be delivered in a continuous micro-dose concentration in a dissolved state that should be sufficient to suppress myopia progression over a prolonged period of time (weeks, months), while maintaining functional pupil constriction and dilation and reading ability.

The present polymeric materials are compatible with human tissue. That is, these materials do not break down in situ, there is no absorption of the materials, there is no deleterious action on the sensitive tissues in the area of placement and the device can be retained on the surface of the eye, over a prolonged period of time.

The polymers suitable for the purpose of any of the exemplary devices disclosed herein include polymers, copolymers and the like, that are prepared and formed into desired shapes by casting, molding, extrusion or other fabrication processes known in the art (U.S. Pat. Appl 20100178315 and U.S. Pat. Appl 20060198892).

According to one exemplary embodiment, polymeric materials are disclosed that are suitable as matrices for the controlled delivery of myopia-suppressing agents. The polymeric material that forms the polymeric matrix or drug carrier comprises alkyl ether segments having the formula:

where $n=2$ to about 10
and $m=1$ to about 20

The alkyl ether segment contains at least one ethylenically unsaturated moiety that can enter into a polymerization reaction and generally has the following structure:

where: P is an ethylenically unsaturated polymerizable group chosen from among

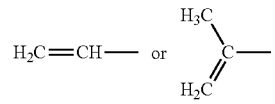

and Y is a spacer group chosen from, but not limited to:
—CO—
—OCO—
—CONHCH$_2$—
—CONHCH$_2$CH$_2$CH$_2$—
—COOCH$_2$CH$_2$NHCOCH$_2$—
—COOCH$_2$CH$_2$NHCH$_2$CH(OH)CH$_2$—
—CH$_2$—
—CH$_2$CH$_2$—
—CH$_2$CH$_2$CH$_2$—
—CH$_2$CH$_2$CH$_2$CH$_2$—
—C$_6$H$_4$—
—C$_6$H$_4$CH$_2$—
—COOCH$_2$CH(OH)CH$_2$—
—COOCH$_2$CH$_2$—
—COOCH$_2$CH$_2$OCH$_2$CH$_2$— and
—COOCH$_2$CH$_2$NHCO—

Examples of ethylenically unsaturated alkyl ether compositions include, but are not limited to:

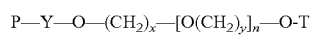

where: P is an ethylenically unsaturated polymerizable group;
Y is a spacer group;
T is a terminal group, which is an alkyl group or a P—Y group x is an integer from 2 to about 6
y is an integer from 2 to about 8
n is an integer 0 to about 20

Exemplary alkyl ether containing monomers that are suitable for use in the present compositions include:

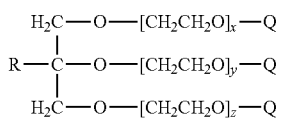

where: Q is independently an alkyl group or P—Y—;
P is an ethylenically unsaturated polymerizable group;
Y is a spacer group;
R is hydrogen or alkyl;
and at least one Q group is P—Y— and x, y and z are independently integers from 1 to about 20; or

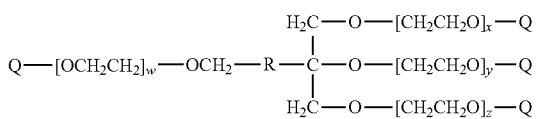

where: Q is independently an alkyl group or P—Y—;
P is an ethylenically unsaturated polymerizable group;
Y is a spacer group;
w, x, y and z are independently integers from 1 to about 50;
and at least one Q group is P—Y—; or

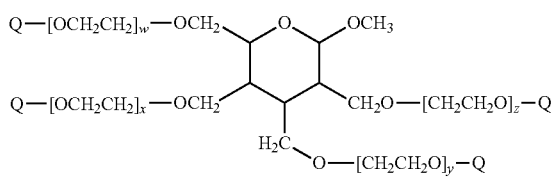

where: Q is independently an alkyl group or P—Y;
P is an ethylenically unsaturated polymerizable group;
Y is a spacer group;
w, x, y and z are independently integers from 1 to about 20;
and at least one Q group is P—Y—; or

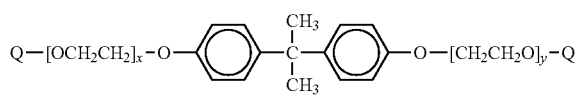

where: Q is independently an alkyl group or P—Y—;
P is an ethylenically unsaturated polymerizable group;
Y is a spacer group;
x and y are independently integers from 1 to about 50;
and at least one Q group is P—Y—.

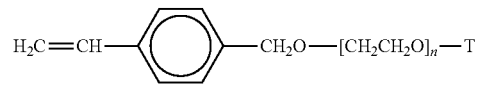

where: T is a terminal group, which is an alkyl group;
n is an integer from 1 to about 20; or

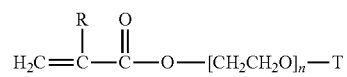

where: T is a terminal group, which is an alkyl group;
n is an integer from 1 to about 20; or

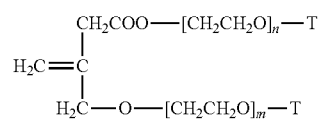

where: R is hydrogen or methyl;
T is a terminal group, which is an alkyl group;
n is an integer from 1 to about 20; or

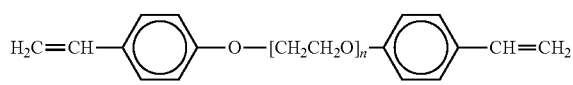

where: T is a terminal group, which is an alkyl group;
n and m are independently integers from 1 to about 20; or

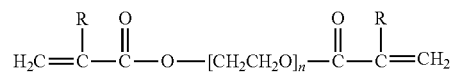

where: n is an integer from 1 to about 20; or

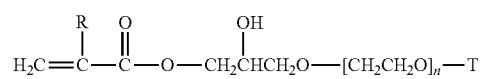

where: R is hydrogen or methyl; and
n is an integer from 1 to about 20.

According to one embodiment, preferred alkyl ether containing monomers include:

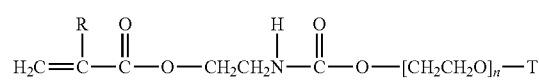

where: R is hydrogen or methyl;
T is a terminal group, which is an alkyl group;
n is an integer from 1 to about 20; or $H_2C{=}\overset{R}{\underset{}{C}}{-}\overset{O}{\underset{}{C}}{-}O{-}CH_2CH_2\overset{H}{\underset{}{N}}{-}\overset{O}{\underset{}{C}}{-}O{-}[CH_2CH_2O]_n{-}T$ where: R is hydrogen or methyl;
T is a terminal group, which is an alkyl group;
n is an integer from 1 to about 20; or

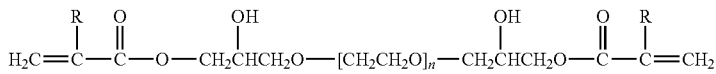

where: R is hydrogen or methyl;
n is an integer from 1 to about 20; or

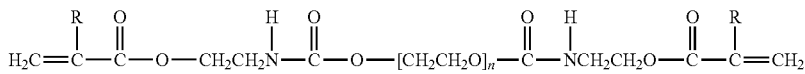

where: R is hydrogen or methyl;
n is an integer from 1 to about 20.
More preferred alkyl ether containing monomers include:

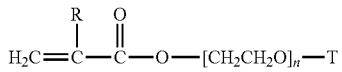

where: R is hydrogen or methyl;
T is a terminal group, which is an alkyl group;
n is an integer from 1 to about 20; or

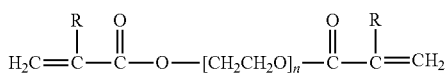

where: R is hydrogen or methyl; and
n is an integer from 1 to about 20.
Most preferred alkyl ether containing monomers include:
Methoxy ethyl acrylate and methacrylate
Methoxy propyl acrylate and methacrylate
Methoxy butyl acrylate and methacrylate
Methoxy ethoxy ethyl acrylate and methacrylate
Ethoxy ethyl acrylate and methacrylate
Ethoxy ethoxy ethyl acrylate and methacrylate
Triethylene glycol monomethyl ether acrylate and methacrylate
Di(ethylene glycol) 2-ethylhexyl ether acrylate and methacrylate
Ethylene glycol diacrylate and dimethacrylate
Diethylene glycol diacrylate and dimethacrylate
Triethylene glycol diacrylate and dimethacrylate
Tetraethylene glycol diacrylate and dimethacrylate
Polyethylene glycol diacrylate and dimethacrylate
1,4 butanediol diacrylate and dimethacrylate
Di(1,4 butanediol) diacrylate and dimethacrylate
Tri(1,4 butanediol) diacrylate and dimethacrylate
Tetra(1,4 butanediol) diacrylate and dimethacrylate
Poly(1,4 butanediol) diacrylate and dimethacrylate
Also of use are macromers prepared from polyalkylether diols. The diol is reacted with 2 mole equivalents of a diisocyanate such as diisophorone diisocyanate or toluene diisocyanate. This prepolymer is end-capped with an ethylenically reactive group. The vinylic reactive macromers described here are useful in the practice of this invention.

In preparing the polymeric matrices and membranes, it is often preferable to form copolymers of the alkyl ether containing monomer with one or more comonomers. The drug release profile from these copolymer matrices can be altered considerably by the choice of comonomer(s). For example, use of a hydrophobic comonomer(s) with the alkyl ether containing monomer will form matrices that will be compatible with drugs that are hydrophobic. On the other hand, use of a hydrophilic comonomer(s) will produce matrices and membranes that are more compatible with hydrophilic drugs. The release profile of a drug from matrices described in this invention can also be altered by the degree of crosslinking. Matrices with higher degrees of crosslinking will retard the diffusion of the drug from the matrix, thus providing slower release rates.

The monomers, which can be present in the polymers used to form a drug release device, can be any copolymerizable vinyl monomer. The following are representative groups of comonomers that can be employed and serve as examples only and are not intended to limit the scope of the invention.

Suitable comonomers include alkyl acrylates and methacrylates, especially $C_1$-$C_{20}$ alkyl acrylates and $C_1$-$C_{20}$ alkyl methacrylates, such as methyl methacrylate, ethyl methacrylate, methyl acrylate, butyl methacrylate, butyl acrylate, 2-ethylhexyl acrylate, 2-ethylhexyl methacrylate and the like; alkonoic vinyl esters, especially $C_1$-$C_6$ alkanoic vinyl esters such as vinyl acetate, vinyl butyrate and the like; alkenes, especially $C_1$-$C_8$ alkenes, including ethylene, 1-butene, 1-hexene, and the like; styrenes, especially styrene and alpha-methyl styrene; vinyl ethers, especially $C_1$-$C_6$ alkyl vinyl ethers, including methyl vinyl ether, ethyl vinyl ether and butyl vinyl ether, and the like; dialkyl maleates, fumarates or itaconates, especially $C_1$-$C_6$ dialkyl maleates, fumarates or itaconates, including dimethyl maleate, dimethyl fumarate, diethyl maleate, dimethyl itaconate and the like; allyl ethers and esters, especially allyl $C_1$-$C_6$ alkyl ethers and allyl $C_2$-$C_6$ alkanoate esters, including allyl methyl ether, allyl ethyl ether, allyl acetate and the like; perfluoro $C_3$-$C_6$ alkyl acrylates or methacrylates; perfluoroalkoxylated bis-acrylates or -methacrylates; poly- or oligoalkylsiloxane acrylates or methacrylates, and the like.

Also, minor amounts of a crosslinking agent, to alter drug release characteristics, stability and the mechanical properties of the polymer are generally employed. Suitable crosslinking agents include, for example, $C_2$-$C_6$ alkylene, dimethacrylates and acrylates, glycerine trimethacrylate; allyl acrylate or methacrylate, divinyl benzene, poly- or oligoalkylsiloxane di-acrylate or -methacrylate, and the like.

Suitable hydrophilic comonomers are hydroxyl-substituted lower alkyl acrylates and methacrylates, acrylamide, methacrylamide, (lower alkyl)acrylamides and -methacrylamides, N,N-dialkyl-acrylamides, ethoxylated acrylates and methacrylates, polyethyleneglycol-mono (meth) acrylates and polyethyleneglycolmonomethylether-(meth) acrylates, hydroxyl-substituted (lower alkyl)acrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, amino(lower alkyl)-(where the term "amino" also includes quaternary ammonium), mono(lower alkylamino)(lower alkyl) and di(lower alkylamino)(lower alkyl)acrylates and methacrylates, allyl alcohol and the like. Preference is given for example, to N-vinyl-2-pyrrolidone, acrylamide, dimethyl acrylamide, methacrylamide, 2-(dimethylamino)ethyl acrylate and methacrylate, 3-(dimethylamino)propyl acrylate and methacrylate, 2-(diethylamino)ethyl methacrylate and methacrylate, 3-(dimethylamino)propyl acrylamide and methacrylamide, hydroxyl-substituted lower alkyl acrylates and methacrylates, hydroxy-substituted (lower alkyl)acrylamides and -methacrylamides and vinylically unsaturated carboxylic acids having a total of 3 to 5 carbon atoms, particularly acrylic and methacrylic acid. Suitable fluorinated monomers include 1,1,2,2-tetrahydroperfluorodecyl acrylate and methacrylate, 1,1,2,2-tetrahydroperfluorooctyl acrylate and methacrylate and 1,1,2,2-tetrahydroperfluorooctyl methacrylamide or acrylamide, 2,2,2-trifluoroethyl acrylate and methacrylate, hexafluoroisopropyl acrylate, hexafluoroisopropyl methacrylate, perfluorocylcohexyl methacrylate, and 2,3,4,5,6-pentafluoro-styrene; the acrylates and methacrylates of fluoroalkyl substituted amido-alcohols, such as of $C_7F_{15}CON(C_2H_5)C_2H_4OH$; of sulfonamido-alcohols, such as of $C_8F_{17}C_8H_4SO_2N(CH_3)$—$C_4H_8OH$ and $C_8C_{17}SO_2N(C_2H_5)$—$C_2H_4OH$; of perfluoroether alcohols, such as of $C_3F_7$—$O(C_3F_6O)_2CF(CF_3)$—$CH_2OH$ or $(CF_3)_2CFO(CF_2CF_2)_2$—$CH_2CH_2OH$; and the acrylates and methacrylate of fluorinated thioether alcohols of structure $CF_3(CF_2)_fCH_2CH_2SCH_2CH_2CH_2OH$; acrylates and methacrylates of sulfonamido-amines, such as of $R_fSO_2NH(CH_3)CH_2CH_2N(CH_3)$—$(CH_2)_3NH$ and $R_fCH_3SO_2NH(CH_2)_2$; of amido-amines, such as of $R_fCONH(CH_2)_2NH_2$; as well as the vinyl monomers obtained by reaction of these aforementioned fluorinated alcohols and amines with 2-isocyanatoethyl acrylate or methacrylate or m-isopropenyl-1,1-dimethylbenzyl isocyanate.

Suitable silicone containing vinyl monomers are oligosiloxanyl-silylalkyl acrylates and methacrylates containing from 2-10 Si-atoms. Typical representatives include: tris (trimethylsiloxy-silyl)propyl (meth)acrylate, triphenyldimethyl-disiloxanylmethyl (meth)acrylate, pentamethyl-disiloxanylmethyl (meth)acrylate, tertbutyl-tetramethyl-disiloxanylethyl (meth)acrylate, methyl-di(trimethylsiloxy) silylpropyl-glyceryl (meth)acrylate; pentamethyldisiloxanyl-methyl methacrylate; heptamethyl-cyclotetrasiloxy methyl methacrylate; heptamethyl-cyclotetrasiloxy-propyl methacrylate; (trimethylsilyl)-decamethyl-pentasiloxy-propyl methacrylate; dodecamethyl pentasiloxypropyl methacrylate.

While copolymerization is a preferred means of tailoring the resulting polymer to provide controlled diffusion of an active agent, the use of plasticizers can also be employed. Incorporation of a plasticizer into the polymeric matrices of this invention will alter the diffusion characteristics of the active agent, increasing its rate of release. This use of plasticizers will also result in altered mechanical properties of the polymeric matrix or membrane. Representative classes of plasticizers that can be employed in the practice of this invention include, but are not limited to; adipates, citrates, maleates, phthalates and trimellitates.

In certain applications of drug delivery, namely delivery, or in certain circumstances ocular delivery, penetration enhancers may be utilized. The penetration enhancers loosen the cell structure of tissue, such as the skin, to allow the active agent to diffuse into the tissue structure more easily. Representative classes of penetration enhancers that can be employed in the practice of this invention include, but are not limited to; sulfoxides, acetamides, formamides, toluamides, pyrrolidones, and higher saturated and unsaturated carboxylic acids. The higher carboxylic acids are of particular interest since they will form an acid/base pair with amine containing drugs such as atropine. As an example, heptanoic acid, octanoic acid, lauric acid, 2-ethylhexanoic acid, sorbic acid and elaidic acid are useful in this function.

Polymerization of the alkyl ether containing monomers of this invention alone, or with comonomers, may be carried out by employing initiators which generate free-radicals on application of an activating energy as is conventionally used in the polymerization of ethylenically unsaturated monomers. Included among free-radical initiators are the conventional thermally activated initiators such as azo compounds, organic peroxides and organic hydroperoxides. Representative examples of such initiators include benzoyl peroxide, tertiary-butyl perbenzoate, diisopropyl peroxydicarbonate, cumene hydroperoxide, azobis(isobutryonitrile), and the like. Generally, from about 0.01 to 5 percent by weight of thermal initiator is used.

UV-initiated polymerization is carried out using photoinitiators. Such initiators are well known and have been described, for example, in polymerization art, e.g., Chapter II of "Photochemistry" by Calvert and Pitts, John Wiley & Sons (1966). The preferred initiators are photoinitiators, which facilitate polymerization when the composition is irradiated. Representative examples of such initiators include acyloin and derivatives thereof, such as benzoin, benzoin methyl ether, benzoin ethyl ether, benzoin isopropyl ether, benzoin isobutyl ether and α-methylbenzoin; diketones such as benzil and diacetyl, etc.; ketones such as acetophenone, α,α,α-tribromoacetophenone, α,α-diethoxy-acetophenone (DEAP), 2-hydroxy-2-methyl-1-phenyl-1-propanone, o-nitro-α,α,α-tribromoacetophenone, benzophenone and p,p'-tetramethyldiaminobenzophenone; α-acyloxime esters such as benzil-(O-ethoxycarbonyl)-α-monoxime; ketone/amine combinations such as benzophenone/N-methyldiethanolamine, benzophenone/tributylamine and benzophenone/Michler's ketone; and benzil ketals such as benzil dimethyl ketal, benzil diethyl ketal and 2,5-dichlorobenzil dimethyl ketal. Normally, the photoinitiator is used in amounts ranging from about 0.01 to 5% by weight of the total composition.

The preferred manufacturing process for producing the drug delivery matrix devices of this invention is cast molding utilizing the alkylene oxide containing compositions described herein. In this process a monomer(s), oligomer or resins are placed in a plastic casting mold bearing the geometry of the ocular device. In the case of an ocular device polypropylene casting molds are preferred. Most preferred is a polypropylene resin with a melt flow index above 20. One polypropylene resin is Exxon PP1105E, which has a melt flow index of 34 g/10 min. With melt flows above 20 gm/10 min intricately shaped casting molds can be injection molded with excellent replication of part dimensions using modern CAD/CAM technology and engineering. Other resins such as polystyrene, polyester, polymethylpentene, polyolefins to name a few are also useful to produce casting molds.

Thermal, UV or visible light exposure or a combination of both polymerizes the monomer(s), oligomer or resin. The polymerization process can be carried out at low temperatures preferably in the 25 to 80° C. range. When the device matrix is prepared from ethylenically unsaturated monomers it is preferable to employ a UV initiator and UV polymerization process. The acrylic and methacrylic families of monomers are preferred to construct the device matrix In the applicant's present case, the preferred carrier or matrix compositions are elastomeric materials that do not uptake water to any significant degree and therefore are not hydrogels. This distinction from hydrogels is very important because the myopia-suppressing drug is incorporated in its non-water soluble basic form, which can complex with acidic monomers that become fixed after polymerization. Because the matrix environment is hydrophobic and includes multiple immobilized carboxylic acid functions, the drug diffuses slowly through the polymerized device, to the eye. The rate of diffusion of the drug can be modified by drug concentration, acidic moiety content, by the polymer composition, or by additives, such that the release kinetics of the drug can be adjusted to provide sustained-release of the active at low concentrations over a long period of time [weeks, months]. Incorporated into the device, as described herein, the delivery of the drug can be optimized to provide concentrations that should be sufficient to suppress myopia progression, while minimizing both local and systemic adverse effects. This tightly controlled yet continually sustained range of dosing provides three advantages in a novel manner. The first is that enough drug is delivered to effectively decrease the rate of myopia progression. The second is that the pupil and focusing functions are maintained throughout the treatment period, without repeated daily or more frequent occurrences of fixed or excessively dilated pupils and inability to see up close that occur with all concentrations of atropine eye drops, except for those that are marginally effective in treating myopia. Such undesirable drop treatment effectively transmogrifies the children into the status of adult patients who just had an incapacitating dilated eye exam. Atropine eye drop studies have demonstrated that the children do not tolerate these side effects of standard drops, but will tolerate lower dose drops that do not excessively limit their pupil and focusing functions. However, the lower dose drops are not as effective in treating the myopia progression. The third advantage of long-duration micro-dosing is that, by avoiding repeated and prolonged excessive pupillary dilation, UV exposure to the retina and lens would be reduced, limiting UV-induced retinal toxicity, cataract formation, and/or macular degeneration.

The matrix of the device, described herein, is composed of a basic drug that complexes with acidic monomers. After polymerization, the monomers are fixed, while the drug still is capable of diffusing diffuse through the device matrix. The matrix is somewhat similar to that described by J. Liao et al WO2014151492, in the preparation of a transdermal device, by Galin et al U.S. Pat. No. 5,612,027 in their fluid (i.e., not solid) composition for maintaining the integrity of the anterior chamber of the eye, and by Houze et al US application US20020058068A1 in their dermal composition.

What distinguishes this invention, from these compositions, as well as other prior art, is that the matrix is chemically fine-tuned to produce a topical device, which fits the sclera of the eye to deliver micro-concentrations of a myopia-suppressing agent; this low-concentration drug delivery targets ocular growth receptors, while minimizing the action of the drug on non-target receptors, thereby reducing adverse effects. For example atropine, a drug presented in our specification, is one such myopia-suppressing agent. This myopia treatment drug is commonly available as an eye drop solution product. The atropine is utilized as the sulphate salt to allow ready solubility in an aqueous solution. Atropine sulfate dissolves in a limited number of organic solvents and therefore would not be soluble in many of the monomers called out in the present application. However, the atropine free base is quite soluble in an organic medium such as acrylic monomers. For that reason, the applicants provided a polymer matrix for atropine free base that consists mostly of a balance of hydrophilic monomer and hydrophobic monomer to control the drug release kinetics. The applicants developed an internal acid-base complex that provides a useful method of further control over the rate of drug release, allowing for exceptionally long durations of drug delivery of micro-doses of atropine into the eye to treat myopia progression. In the case of atropine free base, the polymer carrier matrix is formulated to contain methacrylic acid or acrylic acid. The molar amount of methacrylic acid to atropine free base determines the duration of release. When methacrylic acid is polymerized into the carrier matrix it is distributed uniformly throughout the polymer structure. The acid groups are then fixed in place and cannot migrate. The atropine free base is also dispersed uniformly throughout the carrier since it is in the dissolved state. When prepared the solid carrier matrix will have atropine free base complexed, or associated, with the acid groups in a static state. Once the ocular device is introduced into the eye it encounters the tear fluid. This sets up a concentration gradient between atropine in the device and the outside fluid environment. This gradient is the driving force for diffusion of the drug from the carrier to the outside environment. Since the acid groups are stationary and the atropine is mobile there is a condition where the acid/drug complex is reversible that is, complexes can break and reform. An atropine molecule will break the complex with one acid group and diffuse until it encounters another acid group where another reversible complex forms. In this manner the atropine will form and break many complexes as it diffuses through the carrier matrix. The net result is a slowing of the atropine release rate depending on the number of complexes formed and broken. The atropine concentration in this matrix can be optimized to attain the long-term drug delivery rate that would affect the desired treatment at the back of the eye and yet maintain adequate pupil and accommodation functions while minimizing local and systemic adverse effects.

EXAMPLE 1

Purification and Storage of Monomers

The following example details the purification of the monomers utilized in exemplary formulations for the present ocular devices. Impurities and inhibitors are removed from the as-received monomers through adsorption onto aluminum oxide. The procedure is as follows: Approximately 2.0 gm of aluminum oxide, activated and basic, is added to a 100 ml wide mouth jar followed by addition of approximately 20 gm of liquid monomer. A magnetic stir bar is added to the jar, the jar is capped, and the contents gently stirred for about two days. The purified monomer is recovered by filtration through a 0.45 micron syringe filter. The purified monomer is stored under refrigeration until use. Methacrylic acid or acrylic acid is vacuum distilled prior to use due to their acidic nature.

EXAMPLE 2

Description, Design and Molding of the Device

This example describes the manufacture of an ocular device of a mass that can be easily handled and replaced by the wearer and can hold enough drug in the matrix material for long-term micro-dose delivery, for example 50-150 mg.

Once a device design is chosen it is necessary to produce tooling to allow the device to be cast molded. The desired device design is computer generated utilizing Solid Works® or similar design program. The resulting design is then utilized to instruct the lathe to generate steel injection mold inserts that will produce casting cups bearing the device design. Casting molds conforming to the desired design are then generated by injection molding utilizing a high melt flow polypropylene. The casting mold consisted of a bottom cup and a fitted top cover that form a tightly sealed unit when assembled. For the purposes of this example two basic casting mold designs were those of large rings to fit rabbit eyes and beagle dog eyes. Additionally various, more sophisticated human topical ocular device designs, as shown in FIGS. 1 and 2, were manufactured using this cast-molding process. It should be understood that the designs of this example are not intended to limit the scope of this invention.

EXAMPLE 3

Preparation of a Standard-Dose (4.5% w/w) Atropine Device Matrix Formulation

An alkyl ether containing methacrylate monomer (Di (ethyleneglycol) ethyl ether methacrylate) is combined with an alkyl ether crosslinking agent (Polyethyleneglycol dimethacrylate), and methacrylic acid, along with a UV initiator, is chosen as the basis for the matrix material that contains the atropine drug. The formulation is weighed out with the desired amount of atropine added then mixed thoroughly to form a clear solution. A formulation with atropine concentrations of 4.5% by weight was made first. By our calculation, atropine, at a concentration of 4.5% w/w polymer, targets drug-release equivalent to an atropine topical drop concentration range of 0.5-1%. The atropine dissolved in this formulation to form a clear solution.

EXAMPLE 4

General Cast Molding Procedure for an Atropine-Loaded Ophthalmic Drug Delivery Matrix Device This Example describes the cast molding of a drug delivery device in the range of 50 to 150 mg mass, containing dissolved atropine. Polypropylene molds produced as described in Example 2 are obtained by injection molding. The polypropylene bottom mold half is filled with the acrylic formulation, such as of Example 3, and the top mold half is mated with the bottom mold half then placed in a clamping fixture. The clamped mold is placed in a 365 nm UV oven and the exposure time set to 10 minutes. The UV dose rate is about 278,000 micro joules per $cm^2$ per minute. The total dosage received in 10 minutes is about 2.78 joules per $cm^2$. After polymerization the devices are removed from the mold and the molds discarded. The acrylic devices are clear and elastomeric and accurately represent the desired design geometry.

EXAMPLE 5

Clinical Evaluation of a Standard-Dose (4.5% w/w) Atropine-Loaded Ophthalmic Drug Delivery Matrix Device Ocular drug delivery devices of this invention containing 4.5 weight percent atropine were cast molded in accordance with EXAMPLE 4. One device weighing 115 mg was evaluated clinically.

This dosing established abundant atropine delivery immediately—enough to increase pupil size vs. the control eye within minutes. Despite removal of the device within an hour, this initially fixed and then excessive dilation persisted for almost a week, and then slowly decreased to normal over two weeks, indicating delivery of the drug with the same clinical effects for which current atropine drops have been used for a hundreds of years (FIG. 4). It took almost a week for the treated eye's pupil to come down to a pupil size differential from the control eye of about two-to-three mm, at which point the glare and focusing issues were no longer symptomatic (FIG. 5). That level of approximately two-to-three mm of tolerable dilation is consistent with the low-dose atropine drop studies. For this experiment, since the initial result was a fixed, dilated pupil in the treated eye, all subsequent measurements of the treated eye pupil diameter were recorded at light levels that established a five mm pupil size in the control eye for comparison.

EXAMPLE 6

Preparation of a Low- and Micro-Dose (0.5 and 0.05% w/w) Atropine Device Matrix Formulation An alkyl ether containing methacrylate monomer (Di (ethyleneglycol) ethyl ether methacrylate) is combined with an alkyl ether crosslinking agent (Polyethyleneglycol dimethacrylate), and methacrylic acid, along with a UV initiator, is chosen as the basis for the matrix material that contains the atropine drug. The formulation is weighed out with the desired amount of atropine added then mixed thoroughly to form a clear solution. For these device formulations we endeavored to bracket with lower amounts of drug loading to release from our matrix chemistry, seeking delivery levels that might improve on the limitations of experimental low dose eye drop concentrations. Two formulations with atropine concentrations of 0.5 and 0.05 weight percent were made.

EXAMPLE 7

Clinical Evaluation of a Low-Dose (0.05% w/w) Atropine-Loaded Ophthalmic Matrix Micro-Dosing Device Ocular drug delivery devices of this invention containing 0.5 and 0.05 weight percent atropine were cast molded in accordance with EXAMPLE 4. The goal of bracketing the sustained release doses was to find the range that caused minimal increase in pupil size, while avoiding a fixed, dilated or even largely dilated pupil. That would indicate mitigation of the associated symptoms of light sensitivity and glare to acceptable levels. We also wanted to avoid excessive effect on accommodation, the eye's ability to change focus from far to near. To manifest the presence of the drug in such a range, over the course of the entire day, this experiment would be expected to establish a steady-state effect of mild pupil dilation, vs. the sporadic, dosing related effect seen with drop instillation. One device of 0.05 weight percent atropine weighing 115 mg was evaluated clinically, with the expectation of establishing the lower end of the dosing bracket with little to no measureable effect on the pupil or accommodation.

The device was worn on one eye, so that the size of the still functioning pupil could be compared to that of the contralateral, untreated control eye. Any differences in size would be easily measurable at all times under various ambient light conditions. Any differences in pupil size between the eyes would thus be due to the presence of drug in the treated eye. This method allowed measurements at all times of days in different places during ordinary activities, and did not have to involve extensive baseline and subsequent measurements under very carefully controlled lighting conditions. Of course, of minor note, the difference between the two eyes measured in this experiment should be slightly higher in terms of magnitude of the treatment effect than would be the difference in pupil size from normal baseline had both eyes been treated. This is because the pupils work together to regulate the total amount of light getting to the back of the eyes. Under any given lighting condition, as the greater amount of light getting into the treated eye does not constrict it as much as it normally would, due to the drug, the other pupil would constrict a little more trying to compensate to adjust the total amount of light getting into both eyes. This is a minor effect but it means that if both eyes were treated, as would be expected for virtually all patients, the increased dilation from the subject's normal pupil diameters under various lighting levels would be a little bit less than the increased dilation we measured for the one treated eye vs. the control eye in this experiment, further manifesting the advantage that the subject of this invention does not excessively dilate the pupils.

We expected the 0.05% to be the "control", or bracketing value that would lead us back towards a higher concentration, just as the drop study of Chia expected the lowest concentration, 0.01%, atropine drop originally to serve as a control but found that it resulted in their best overall treatment balance with side effects (Chia et al, 2012). We therefore tried the 0.05% before trying the 0.5%, expecting little to no measureable treatment effect. Instead we got immediate partial pupil dilation with mild glare symptoms, or blur noted from that eye, for the first day, but no light sensitivity. Such symptoms might be less when both eyes are treated and the pupils are more equal in size. This was followed the second day and beyond by continued greater dilation vs. the control eye, but less so than the first day (FIG. 6), with no glare symptoms for the remainder of the study. The level of drug delivered to the eye yielded a pupil larger than the control eye at every measurement at all light levels, indicating constant delivery of a low amount of drug into the eye. Pupil function was never totally blocked, making the treatment quite comfortable due to the lack of light sensitivity symptoms. Even on the first day when it was the largest, the treated eye pupil remained reactive to changing light conditions, and was not fixed and dilated as expected with conventional drops. The largest amount of drug released would be expected on the first day, due to the inherent burst effect of any matrix release system. Steps can be taken to mitigate this burst, but we did not do this for this lowest-dose experiment. The preservation of pupil function is evident in FIG. 6, as the various values for measured diameter of the control eye was due to measurement in different ambient light levels, and the treated eye also change diameter concordantly, while always remaining larger than the control eye.

Focusing difficulties were not noted throughout the entire study period, although it should be noted that the subject was an adult over fifty with presbyopia, so that reading correction was typically used. However, no particular changes in reading effort from normal, with reading correction or without, were noted.

While we did not establish the lowest possible formulation concentration and drug delivery that would have some effect, this experiment indicates that we are close with the 0.05% and somewhat lower concentrations might also prove useful for this invention.

FIG. 7 shows the pupil size differential between the treated and control eyes. This demonstrates that the treated eye's pupil was always a little larger than that of the control eye, at a variety of ambient light levels, over the entire treatment period.

As described herein, preserving pupillary function and accommodation corresponds to preservation of pupillary function for weeks to months without appreciably excessive effects on pupil dilation or cycloplegia beyond more than 1 day, more preferably 12 hours, and most preferably 4 hours. Preservation of pupillary function corresponds to a dilation in selected conditions, such as room light conditions, that is no more than 3 mm, preferably no more than 2 mm, and most preferably no more than 1 mm different (greater) than a baseline pupil diameter under the same lighting conditions (the control conditions), and provides preservation of near focusing function that corresponds to avoiding the need for additional reading aids in greater than 80% of children treated, more preferably greater than 90% of children treated and most preferably greater than 95% of children treated.

It will therefore be appreciated that, in at least one embodiment, the present invention provides an ocular device for delivery of an anti-muscarinic agent to an eye in a manner that provides sustained, controlled, low dose release in order to preferably maintain a pupil size of about 2 mm to about 3 mm within a baseline, untreated values for most ambient light conditions for the eye being treated, over the course of most or all days of treatment. This is in direct contrast to the application of eye drops that provide a cyclical effect on pupil size in that the pupil size initially opens greatly and then slowly diminishes to a smaller opening then another eye drop repeats this cycle. In contrast, the present device continuously releases and provides steady, controlled pupil size as well as minimizing side effects.

It will further be understood that, as disclosed herein and according to one embodiment, a pupil dilation baseline is a diameter of the pupil as measured in a controlled light setting such as a setting at various specified room light levels ranging from approximately 10-200 foot candles or 100-200 Lux. It will be appreciated that these values are merely exemplary and define a range for an exemplary baseline. The baseline and the observed pupil change of the eye in which the ocular drug delivery device was worn are thus preferably calculated based on room lighting conditions that are normally encountered throughout a typical day. As described herein, functional accommodation relates to maintaining functional accommodation so that near work, such as, reading and studying can be performed comfortably, without the need for additional corrective reading glasses beyond any glasses used prior to treatment, after the present drug delivery device has been placed in the eye and in particular and according to one embodiment, after it has been in the eye for at least 24 hours and at least up to at least 30 days after insertion of the device in the eye. It will be appreciated that functional accommodation can be obtained much quicker and can be on the order of several hours (or even potentially shorter), such as after 4 hrs, 6 hrs, etc., after insertion.

EXAMPLE 8

The device of EXAMPLE 7 was worn continuously for 76 days then submitted for analysis. The remaining drug was removed from the device using the following extraction method. The device was placed in a vial containing 10 ml of isopropanol which was then capped and placed in a 40° C. hot air oven for 9 days. Three unworn devices were also subjected to this extraction procedure to determine the initial atropine content. After extraction the devices were removed from the vials and the solvent retained for atropine analysis. An LC-MS analytical method was utilized for determining the concentration of atropine in the extracts. The analysis of the worn device was carried out in triplicate and the results averaged. It was determined that the ocular device retained 64.8 μg of atropine over the 76 days of wear. From the three unworn devices the atropine contents were averaged to 99.6 From these numbers it was calculated that the worn device had released about 35 μg of atropine or about 35% of its initial atropine content over the 76 days of wear.

In certain embodiments of the present invention, the anti-muscarinic drug is atropine in a concentration range between about 0.001% and about 10% w/w polymer or between 0.001% and about 4.5% w/w, with a preferred concentration range of about 0.01-0.5% w/w and a most preferred concentration range of about 0.03-0.2% w/w. In another embodiment, the anti-muscarinic drug is pirenzepine in a concentration range between about 0.004% and 10% w/w polymer or between about 0.004% and 5% w/w, with a preferred concentration range of about 0.1-3% w/w and a most preferred concentration range of about 0.1 to 1% w/w. In yet another embodiment, the anti-muscarinic drug is racanisodamine, cyclopentolate, homatropine, scopolamine, telenzepine, nuvenzepine or rispenzepine in a concentration range between about 0.001% to 10% w/w polymer or between about 0.001% to 5%. In a further embodiment, the dopamine agonist is dopamine, apomorphine, bromocriptine, quinpirole, or levodopa, in a concentration range between about 0.001% to 10% w/w polymer or between about 0.001% to 5%.

Each of the patents and published patent applications recited herein is expressly incorporated by reference in its entirety.

What is claimed is:

1. A non-degradable, non-invasive scleral topical ocular drug delivery device comprising about 0.01% to about 0.5% w/w of atropine complexed with an immobile acid to form a reversible acid/agent complex that is dispersed throughout an organic phase of a crosslinked hydrophobic non-hydrogel polymer matrix, the cross-linked hydrophobic non-hydrogel polymer matrix being configured to continuously release the atropine from the reversible acid/agent complex over an extended period of at least 7 days at a concentration and rate that at least one of impedes, prevents, and controls myopia progression while preserving pupillary function and accommodation over the extended period, wherein the device is sized, shaped and configured so that it can be worn simultaneously with and independent from a corrective refractive device worn for treatment of myopia including eyeglasses and contact lenses.

2. The device of claim 1, wherein the crosslinked hydrophobic non-hydrogel polymer matrix defines a body that is configured to be held on the sclera of an eye such that the body is free of contact with and spaced away from the cornea of the eye and consequently does not require oxygen permeability and optical qualities.

3. The device of claim 2, wherein the body has an anterior surface and an opposing posterior surface for placement on the sclera, the posterior surface having a concave curved shape that is defined by a base curve shaped to fit the sclera.

4. The device of claim 1, wherein the cross-linked hydrophobic non-hydrogel polymer matrix defines a body having a mass between about 50 mg to about 150 mg.

5. The device of claim 1, wherein the cross-linked hydrophobic non-hydrogel polymer matrix has a water content less than 2% by weight.

6. The device of claim 5, wherein the cross-linked hydrophobic non-hydrogel polymer matrix includes at least 30% by weight of an alkyl ether.

7. The device of claim 6, wherein the alkyl ether is derived from at least one of
a monomer having a formula:

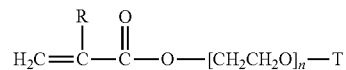

wherein: R is hydrogen or methyl;
T is a terminal group, which is an alkyl group;
n is an integer from 1 to about 20.

8. The device of claim 7, further including at least one of acrylic and methacrylic acid.

9. The device of claim 6, wherein the alkyl ether is derived from at least one of a monomer having a formula:

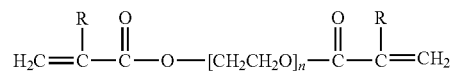

wherein: R is hydrogen or methyl; and
n is an integer from 1 to about 20.

10. The device of claim 1, wherein the cross-linked hydrophobic non-hydrogel polymer matrix is formed of an alkyl ether containing methacrylate monomer; an alkyl ether crosslinking agent; and methacrylic acid which comprises the immobile acid within the cross-linked polymer matrix.

11. The device of claim 10, wherein the alkyl ether containing methacrylate monomer comprises di(ethyleneglycol) ethyl ether methacrylate.

12. The device of claim 10, wherein the alkyl ether crosslinking agent comprises polyethyleneglycol dimethacrylate.

13. The device of claim 1, wherein the atropine is in a concentration range between about 0.02% and about 0.2% w/w polymer.

14. The device of claim 1, wherein the atropine is in a concentration range between about 0.02% and about 0.07% w/w polymer.

15. The device of claim 1, wherein the extended period of time comprises at least 30 days.

16. The device of claim 1, wherein the extended period of time comprises at least 60 days.

17. The device of claim 1, wherein the extended period of time comprises at least 76 days.

18. The device of claim 1, wherein the preservation of pupillary function corresponds to a pupil dilation that is no more than 3 mm greater than a baseline pupil diameter and after the device has been in the eye for at least 24 hours.

19. The device of claim 18, wherein the pupil dilation is predominantly no more than 2 mm greater than the baseline pupil diameter and after the device has been in the eye for at least 24 hours.

20. The device of claim 1, wherein the atropine has a concentration of about 0.05% w/w polymer.

21. A non-degradable topical ocular drug delivery device for at least one of impeding, preventing, and controlling myopia progression, the non-degradable topical ocular drug delivery device comprising:
    a body that is configured to fit and be held on the sclera of an eye, the body being formed of a cross-linked hydrophobic polymer matrix; and
    about 0.01% to about 0.5% w/w of atropine complexed with an immobile acid within the crosslinked hydrophobic non-hydrogel polymer matrix; wherein the cross-linked hydrophobic non-hydrogel polymer matrix is configured to deliver the atropine in sustained, controlled micro doses over an extended period of at least 7 days while maintaining a pupil size increase, over the extended period, of no greater than about 3 mm relative to a pupil dilation baseline after the device has been in the eye for at least 24 hours and up to at least 30 days after insertion of the device in the eye, wherein the device is sized, shaped and configured so that it can be worn simultaneously with and independent from a corrective refractive device worn for treatment of myopia including eyeglasses and contact lenses.

22. The device of claim 21, wherein the pupil size increase is maintained between about 1 mm to about 3 mm relative to the pupil dilation baseline after the device has been in the eye for at least 24 hours and up to at least 30 days after insertion of the device onto the eye.

23. A method for at least one of impeding, preventing, and controlling myopia progression, while maintaining functional pupil constriction and dilation and accommodative ability comprising the steps of:
    inserting the non-degradable non-invasive topical ocular drug delivery device of claim 1 onto an eye; and
    maintaining the non-degradable non-invasive topical ocular drug delivery device on the eye for a predetermined period of time of at least seven days.

24. The device of claim 1, wherein the atropine is loaded into the crosslinked hydrophobic non-hydrogel polymer matrix at an initial quantity of less than 200 μg and the atropine is released from the reversible acid/agent complex at a concentration and rate that results in less than 75 μg of atropine remaining after 76 days of continuous, uninterrupted treatment.

25. The device of claim 1, wherein the atropine is present in a concentration of about 0.05% and whereby at least 25% of the atropine remains in the device after 76 days of continuous wear.

26. The device of claim 1, wherein the atropine is present in a concentration of about 0.05% and the device preserves pupillary function and accommodation after at least 70 days of continuous wear.

\* \* \* \* \*